US009655596B2

(12) United States Patent
Gigi

(10) Patent No.: US 9,655,596 B2
(45) Date of Patent: May 23, 2017

(54) BIOPSY NEEDLE WITH A LATERALLY EXPANDABLE DISTAL PORTION

(71) Applicant: Arch Medical Devices Ltd., Katzrin (IL)

(72) Inventor: Igal Gigi, Givataim (IL)

(73) Assignee: Arch Medical Devices Ltd., Rishpon (IL)

( * ) Notice: Subject to any disclaimer, the term of this patent is extended or adjusted under 35 U.S.C. 154(b) by 0 days.

(21) Appl. No.: 14/178,336

(22) Filed: Feb. 12, 2014

(65) Prior Publication Data

US 2014/0163418 A1    Jun. 12, 2014

Related U.S. Application Data

(63) Continuation-in-part of application No. PCT/IL2013/050402, filed on May 8, 2013.

(60) Provisional application No. 61/645,166, filed on May 10, 2012, provisional application No. 61/755,499, filed on Jan. 23, 2013.

(51) Int. Cl.
*A61B 10/00* (2006.01)
*A61B 10/02* (2006.01)
*A61B 10/04* (2006.01)

(52) U.S. Cl.
CPC ...... *A61B 10/0266* (2013.01); *A61B 10/0233* (2013.01); *A61B 10/04* (2013.01)

(58) Field of Classification Search
CPC ............ A61B 10/0275; A61B 10/0266; A61B 2010/0208
USPC ........................................ 600/562, 564, 467
See application file for complete search history.

(56) References Cited

U.S. PATENT DOCUMENTS

| 2,822,808 | A | 2/1958 | Boone |
| 3,007,471 | A | 11/1961 | McClure, Jr. |
| 3,289,669 | A | 12/1966 | Dwyer et al. |
| 3,844,272 | A | 10/1974 | Banko |

(Continued)

FOREIGN PATENT DOCUMENTS

| EP | 1203566 | 5/2002 |
| FR | 2828088 | 2/2003 |

(Continued)

OTHER PUBLICATIONS

International Search Report and the Written Opinion Dated Sep. 14, 2010 From the International Searching Authority Re. Application No. PCT/IB2010/051289.

(Continued)

*Primary Examiner* — Daniel Cerioni

(57) ABSTRACT

A tissue sampling apparatus and method are disclosed. Some embodiments comprise a biopsy needle having a laterally expandable distal portion comprising spines which move away from each other when unconstrained and which move towards each other when constrained to do so a sheath. In some embodiments said spines comprise inward-pointing teeth designed to catch tissue samples when said needle retracted from tissue. A method of use comprises providing such a needle within a sheath, advancing the sheath to near a sampling site, advancing needle beyond sheath to expand the expandable portion, retracting needle into sheath so that the expandable portion collapses and tissue samples are trapped between the teeth and spines, and removing the needle and the samples it contains from the body.

30 Claims, 44 Drawing Sheets

(56) References Cited

U.S. PATENT DOCUMENTS

| | | | |
|---|---|---|---|
| 4,243,049 A | 1/1981 | Goodale et al. | |
| 4,724,840 A | 2/1988 | McVay et al. | |
| 4,989,614 A | 2/1991 | Dejter, Jr. et al. | |
| 5,301,684 A | 4/1994 | Ogirala | |
| 5,357,974 A | 10/1994 | Baldridge | |
| 5,527,331 A | 6/1996 | Kresch et al. | |
| 5,527,340 A | 6/1996 | Vogel | |
| 5,794,626 A | 8/1998 | Kieturakis | |
| 6,080,115 A | 6/2000 | Rubinstein | |
| 6,228,039 B1 | 5/2001 | Binmoeller | |
| 6,632,182 B1 | 10/2003 | Treat | |
| 6,752,767 B2 | 6/2004 | Turovskiy et al. | |
| 6,936,014 B2 | 8/2005 | Vetter et al. | |
| 7,052,501 B2 | 5/2006 | McGuckin, Jr. | |
| 7,473,232 B2 | 1/2009 | Teague | |
| 7,951,089 B2 | 5/2011 | Miller | |
| 2001/0001811 A1 | 5/2001 | Burney et al. | |
| 2001/0005778 A1 | 6/2001 | Ouchi | |
| 2002/0022788 A1 | 2/2002 | Corvi et al. | |
| 2002/0022850 A1* | 2/2002 | McGuckin, Jr. | 606/114 |
| 2002/0183758 A1 | 12/2002 | Middleton et al. | |
| 2005/0228403 A1 | 10/2005 | Ho et al. | |
| 2007/0016100 A1* | 1/2007 | Miller | 600/567 |
| 2007/0142852 A1* | 6/2007 | Lee et al. | 606/170 |
| 2008/0114364 A1 | 5/2008 | Goldin et al. | |
| 2009/0036936 A1 | 2/2009 | Solsberg et al. | |
| 2010/0076303 A1 | 3/2010 | McKinley | |
| 2010/0268272 A1* | 10/2010 | Kirsch et al. | 606/228 |
| 2010/0317996 A1 | 12/2010 | Dillon | |
| 2012/0022396 A1* | 1/2012 | Gigi | 600/564 |
| 2012/0022568 A1* | 1/2012 | Koblish et al. | 606/185 |
| 2013/0046201 A1* | 2/2013 | Stanley et al. | 600/567 |

FOREIGN PATENT DOCUMENTS

| | | |
|---|---|---|
| JP | 10-179593 | 7/1998 |
| WO | WO 95/20914 | 8/1995 |
| WO | WO 02/062226 | 8/2002 |
| WO | WO 2006/015302 | 2/2006 |
| WO | WO 2013/168166 | 11/2013 |

OTHER PUBLICATIONS

International Search Report and the Written Opinion Dated Aug. 27, 2013 From the International Searching Authority Re. Application No. PCT/IL2013/050402.

Patents Act 1977: Combined Search and Examination Report Under Sections 17 and 18(3) Dated Jul. 27, 2009 From the Intellectual Property Office of the United Kingdom Re. Application No. GB0905512.0.

International Preliminary Report on Patentability Dated Nov. 20, 2014 From the International Bureau of WIPO Re. Application No. PCT/IL2013/050402.

Covidien "SuperDimension™ Triple Needle Cytology Brush", Product Sheet, Covidien AG, 2014.

Supplementary European Search Report and the European Search Opinion Dated Feb. 17, 2016 From the European Patent Office Re. Application No. 13787135.6.

\* cited by examiner (measurements in mm)

(measurements in mm)

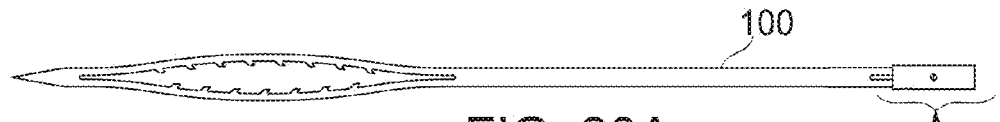
FIG. 20A
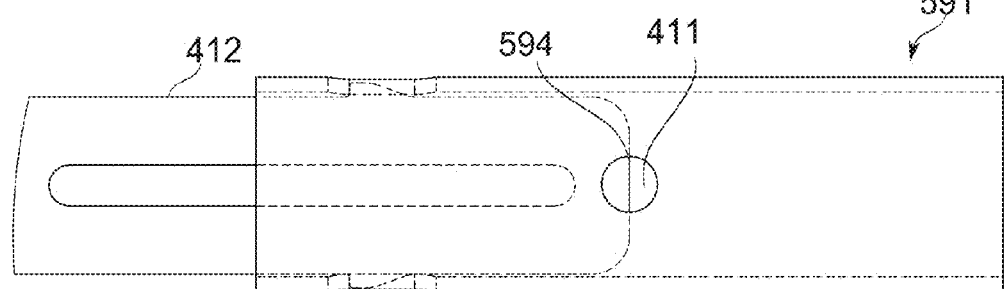
FIG. 20B
FIG. 20C
FIG. 20D
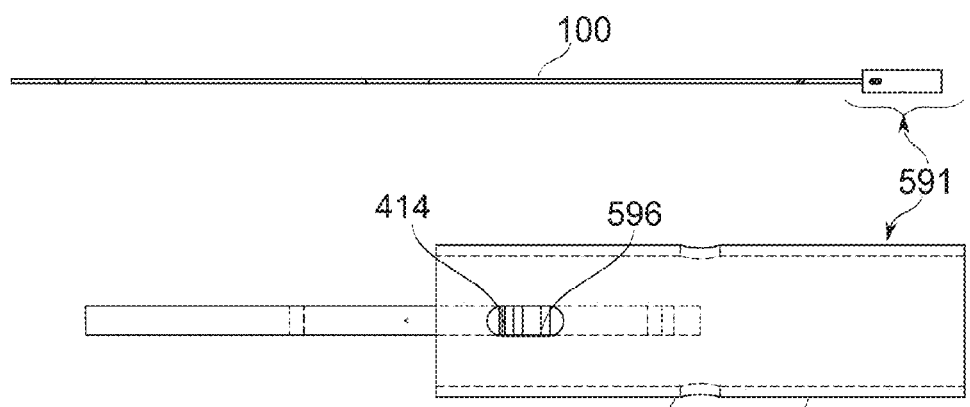
FIG. 20E

BIOPSY NEEDLE WITH A LATERALLY EXPANDABLE DISTAL PORTION

RELATED APPLICATIONS

This application is a continuation-in-part (CIP) of PCT Patent Application No. PCT/IL2013/050402 having International filing date of May 8, 2013, which claims the benefit of priority under 35 USC §119(e) of U.S. Provisional Patent Application Nos. 61/645,166 filed on May 10, 2012 and 61/755,499 filed on Jan. 23, 2013. The contents of the above applications are all incorporated herein by reference.

FIELD AND BACKGROUND OF THE INVENTION

The present invention, in some embodiments thereof, relates to a device and method for collecting tissue samples, and, more particularly, but not exclusively, to biopsy needles introduced into the body within a sheath.

Sampling of body tissues is often required to help in diagnosis and disease staging of patients. Numerous tools and devices for such purpose have been disclosed. Many comprise a narrow elongated guide or sheath through which a sampling needle or blade is advanced to take a sample, and then retracted.

On Mar. 24, 2010 the Applicant of the current application filed a PCT application published under International Publication Number WO 2010/113080. That application is referred to as "PCT '080" herein.

PCT '080 presents inter alia a variety of configurations of blades (generally labeled blade 10 in the application) which comprise a sharp anterior portion 12 designed for penetrating into tissue, and one or more recesses or notches which comprise sharp or pointed edges capable of cutting and ripping-off some of the tissue into which blade 10 penetrates, which notches or recesses are generally labeled recesses 16 or notches 16 in PCT '080. These notches or recesses are shown as positioned on the sharp edges of blade 10 as shown in FIGS. 1A, 1B, 1C, and 1G, and on an otherwise flat side of blade 10 in FIGS. 1D, 1E, and 1F of PCT '080.

SUMMARY OF THE INVENTION

The present invention, in some embodiments thereof, relates to a biopsy needle for removing tissue samples from within a body, e.g. samples to be used for pathological examinations or other examinations of the tissue. The present invention, in some embodiments thereof, relates particularly to biopsy needles having a laterally expandable distal portion which comprises a plurality of longitudinal elements (called "spines" herein) operable to laterally expand away from each other into an "open" configuration when unconstrained, and to approach each other to form a "closed" configuration when constrained to do so. In some embodiments, spines laterally expand away from each other into an "open" configuration when unconstrained, and approach each other to form a "closed" configuration when constrained to do so.

A configuration is considered "open" when spines move away from each other to a distance which allows at least body tissue adjacent to the needle to penetrate into a volume defined between (or among) the laterally expanded spines. A configuration is considered closed when the spines and/or teeth on the spines are close enough to each other to catch and hold tissue between them while the needle is moved within the body.

In some embodiments at least some of these longitudinal elements comprise "teeth" which grasp (and/or cut and/or tear) tissue samples when the needle is advanced and/or retracted and/or changed from open to closed configuration. In some embodiments the teeth are oriented to point towards each other and/or towards other teeth-supporting elements (called "spines" herein), rather than pointing outwards from the needle as was taught in PCT '080. Teeth which point towards other teeth and/or spines of the device are referred to as "inward-pointing teeth" herein.

In some embodiments a containing sheath constrains a needle such as the needle described in the preceding paragraph, forcing the needle into a closed configuration when the needle is contained or partially contained within the sheath.

In some embodiments a needle in a sheath and in what is called herein a "closed configuration" is advanced towards a sampling site, and then a distal portion of the needle is extended from the sheath into body tissues. Advancing the expandable portion of the needle beyond a distal end of the sheath causes the expandable portion to expand, putting the needle into what is called herein an "open configuration." When the distal portion of the needle is then retracted into the sheath (and/or when the sheath is advanced over that distal portion), forcing the needle back into closed configuration, body tissue may be captured between the spines and/or between the teeth of the needle. With the needle again in closed configuration within the sheath, captured tissue is held and protected both by interior surfaces of the spines and surfaces of the teeth and by the sheath. The needle and sheath (or only the needle) can then be extracted from the body and the captured tissue garnered for pathological or other examination.

According to an aspect of some embodiments of the present invention, there is provided a biopsy needle comprising a laterally expandable distal portion.

According to an aspect of some embodiments of the present invention, there is provided a biopsy needle comprising a laterally self-expanding distal portion.

According to some embodiments of the invention, the needle comprises a sharp distal end capable of penetrating tissue.

According to some embodiments of the invention, the laterally expandable distal portion, once laterally expanded to an open configuration, is laterally contractible to a closed configuration.

According to some embodiments of the invention, the laterally expandable portion in an open configuration is shaped to allow at least some tissue located in a vicinity of the expandable portion to move into the expandable portion.

According to some embodiments of the invention, the expandable portion is laterally contractible from the open configuration to trap and hold the tissue.

According to some embodiments of the invention, the expandable portion contracts when the needle is retracted from tissue into which it had penetrated.

According to some embodiments of the invention, the expandable portion contracts when the relative position of the needle and a sheath changes, covering a portion of the needle with a distal portion of the sheath.

According to some embodiments of the invention, the needle comprises a base end with a releasable catch configured for tool-free mounting and unmounting to a receiving part.

According to some embodiments of the invention, the base end is flattened.

According to some embodiments of the invention, the expandable portion comprises a plurality of spines moveable toward and away from each other along at least a portion of their length.

According to some embodiments of the invention, the spines are joined at their distal end and at their proximal end.

According to some embodiments of the invention, the spines distance themselves from each other when the expandable portion is laterally unconstrained, and approach each other when the expandable portion is laterally constrained.

According to some embodiments of the invention, the needle comprises teeth along at least one of the spines.

According to some embodiments of the invention, at least some of the teeth along the at least one spine protrude into an interior volume defined by the spines when the spines are distanced from each other in an open configuration.

According to some embodiments of the invention, at least some of the teeth are so oriented as to have a sharp edge facing in a proximal direction, so as to catch and hold tissue when a distal portion of the needle is retracted from tissue into which it has been inserted.

According to some embodiments of the invention, the spines are operable to trap and hold tissue when the needle is inserted into tissue and is constrained to change from open to closed configuration.

According to some embodiments of the invention, the needle comprises more than two spines.

According to some embodiments of the invention, the needle comprises a longitudinal passageway extending from a distal end of the spines and ending in a distal orifice.

According to some embodiments of the invention, the needle has a bendable distal portion.

According to some embodiments of the invention, the expandable portion contracts when the needle is retracted into a distal portion of a sheath.

According to some embodiments of the invention, the expandable portion contracts when a distal portion of a sheath is advanced over the expandable portion.

According to some embodiments of the invention, the spines approach each other when constrained to do so by a sheath advancing along the needle until it at least partially encloses at least a part of the laterally expandable portion of the needle.

According to some embodiments of the invention, the spines approach each other when constrained to do so by a sheath when at least a part of the distally expandable portion of the needle is retracted into the sheath, thereby enclosing at least a part of the laterally expandable portion of the needle within the sheath.

According to some embodiments of the invention, the spines, when constrained to approach each other, define a volume capable of holding a tissue sample.

According to some embodiments of the invention, at least some of the teeth are backward-pointing teeth which catch tissue when the needle is retracted from tissue into which it is inserted.

According to some embodiments of the invention, all teeth along the spines are backward-pointing and catch tissue only during retraction of the needle from the tissue.

According to some embodiments of the invention, the teeth along the first one of the spines have sharp portions facing another of the spines.

According to some embodiments of the invention, at least some of the teeth are backward-pointing teeth which catch tissue during retraction of the needle, and at least some of the teeth are inward-pointing teeth having sharp portions which face an internal volume of the needle defined by the spines when the expandable distal portion of the needle is in open configuration.

According to some embodiments of the invention, the spines define an internal volume of the needle when the needle is in closed configuration, and the volume is sufficiently large to contain tissue samples useful for tissue pathology examinations.

According to some embodiments of the invention, at least most teeth of the needle have sharp portions which face and point towards other portions of the needle.

According to some embodiments of the invention, at least some of the teeth are designed to catch tissue during retraction of the needle from tissue into which it is inserted.

According to some embodiments of the invention, at least some of the teeth comprise a recessed portion capable of holding tissue when the needle is in closed configuration.

According to some embodiments of the invention, the needle comprises two spines attached at their proximal and distal ends and comprising medial portions capable of moving away from each other into an open configuration and also capable of being positioned near each other in a closed configuration.

According to some embodiments of the invention, the medial portions of the spines move away from each other when unconstrained, but which may be constrained to approach each other to form a closed configuration.

According to some embodiments of the invention, the more than two spines define a volume capable of holding body tissue when the spines are in closed configuration, the spines then being near each other along their length.

According to some embodiments of the invention, the more than two spines define a volume capable of holding body tissue when the spines are in closed configuration, the spines then touching each other along at least a part of their length.

According to some embodiments of the invention, the needle comprises three spines.

According to some embodiments of the invention, the needle comprises four spines.

According to some embodiments of the invention, the needle comprises at least 3 spines and further comprises a longitudinal passageway ending in a distal orifice.

According to some embodiments of the invention, the needle comprises two spines.

According to an aspect of some embodiments of the present invention, there is provided a tissue sampling apparatus which comprises: (a) a biopsy needle which comprises a laterally expandable distal portion; and (b) a sheath sized to contain at least a distal portion of the needle; such that (c) the needle is slideable distally and proximally within the sheath; and (d) the needle tends to assume an open or closed configuration depending on where the expandable distal portion of the needle is positioned within the sheath.

According to some embodiments of the invention, the needle tends to assume an open configuration when the expandable distal portion extends beyond the sheath, and the expandable distal portion is constrained to assume a closed configuration when the expandable distal portion of the needle is positioned within the sheath.

According to some embodiments of the invention, the sheath comprises an elongated sheath body having an interior lumen with an arcuate slot forming a continuum between an interior lumen of the sheath and an exterior aperture disposed laterally on the sheath body.

According to some embodiments of the invention, one or more walls of the lumenal surface of the sheath are formed with protrusions having heights sufficient to lift at least a portion of the needle away from adjacent portions of the lumenal surface.

According to some embodiments of the invention, protrusions of facing walls of the lumenal surface are arranged in staggered alternation along the length of the lumenal surface.

According to some embodiments of the invention, the apparatus comprises: a sheath head at a distal end of the sheath; the sheath head comprising a substantially tubular body; wherein the wall of the body comprises at least one flap cut from the body of the sheath head, and formed to protrude into a lumen defined by the body, such that the at least one flap comprises at least one guide protrusion contacted by the needle upon passage of a portion of the needle through the body.

According to some embodiments of the invention, the guide protrusion comprises a bearing surface having a polymer resin coating.

According to some embodiments of the invention, the at least one guide protrusion comprises at least two guide protrusions protruding into the lumen from opposite sides of the lumen.

According to some embodiments of the invention, the sheath head comprises an angle guide positioned at a distal end thereof; and the needle is constrained by contact with the angle guide to exit the sheath head at an angle oblique to the longitudinal axis of the sheath head.

According to some embodiments of the invention, the oblique exit angle is also determined by contact with a guide protrusion on a side of the needle opposite the angle guide.

According to some embodiments of the invention, the angle guide comprises a flap cut from the body of the sheath head.

According to some embodiments of the invention, the needle comprises a bendable distal portion.

According to some embodiments of the invention, the lumenal surface of the sheath is undulated, forming protrusions.

According to some embodiments of the invention, at least one of any protrusions in the form of the lumenal surface falls away along a steeper grade on the side opposite the side first approached by the tip of the needle during extension of the needle than on the first-approached side.

According to some embodiments of the invention, protrusions in the form of the lumenal surface are arranged to avoid mutual reinforcement of the tendency of each protrusion to impede passage of the needle.

According to some embodiments of the invention, protrusions in the form of the lumenal surface are arranged at non-constant distances from one another.

According to an aspect of some embodiments of the present invention there is provided a method for capturing tissue samples from within a body, comprising: (a) advancing a sheath containing a biopsy needle having a laterally expandable distal portion to a vicinity of a tissue; (b) extending the distal portion of the needle beyond a distal end of the sheath, thereby causing the laterally expandable distal portion of the needle to assume an open configuration; and (c) causing the sheath to cover at least a part of the laterally expandable distal portion, thereby causing the laterally expandable distal portion to assume a closed configuration, thereby trapping body tissue within the distal portion; (d) retracting all of the distal portion into the sheath; and (e) retracting the needle, containing the tissue samples, from the body.

According to some embodiments of the invention, the method further comprises causing the sheath to cover at least a part of the laterally expandable distal portion by advancing the sheath over at least a part of the laterally expandable distal portion.

According to some embodiments of the invention, the method further comprises causing the sheath to cover at least a part of the laterally expandable distal portion by retracting the needle into the sheath, until the sheath covers at least a part of the laterally expandable distal portion.

According to an aspect of some embodiments of the present invention, there is provided a method for capturing tissue samples from within a body, comprising: (a) advancing a sheath at least partially containing a biopsy needle having a laterally expandable distal portion to a vicinity of a tissue; (b) causing a distal portion of the sheath to change how much of at least a part of the laterally expandable distal portion it covers, thereby constraining the expandable portion to assume a closed configuration, thereby trapping tissue within the distal portion; and (c) retracting the needle, containing the tissue samples, from the body.

According to some embodiments of the invention, causing a distal portion of the sheath to cover at least a part of the laterally expandable distal portion of the needle thereby constrains the expandable portion to assume a closed configuration, thereby trapping tissue within the distal portion.

According to some embodiments of the invention, the method comprises extending the distal portion of the needle beyond a distal end of the sheath to cause the laterally expandable distal portion of the needle to assume an open configuration prior to the trapping of tissue.

According to some embodiments of the invention, the method comprises retracting all of the distal portion of the needle into the sheath.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 20A-20E are schematic views of exemplary attachment structures in detail, according to some exemplary embodiments of the present invention;

DESCRIPTION OF SPECIFIC EMBODIMENTS OF THE INVENTION

Figure 1:
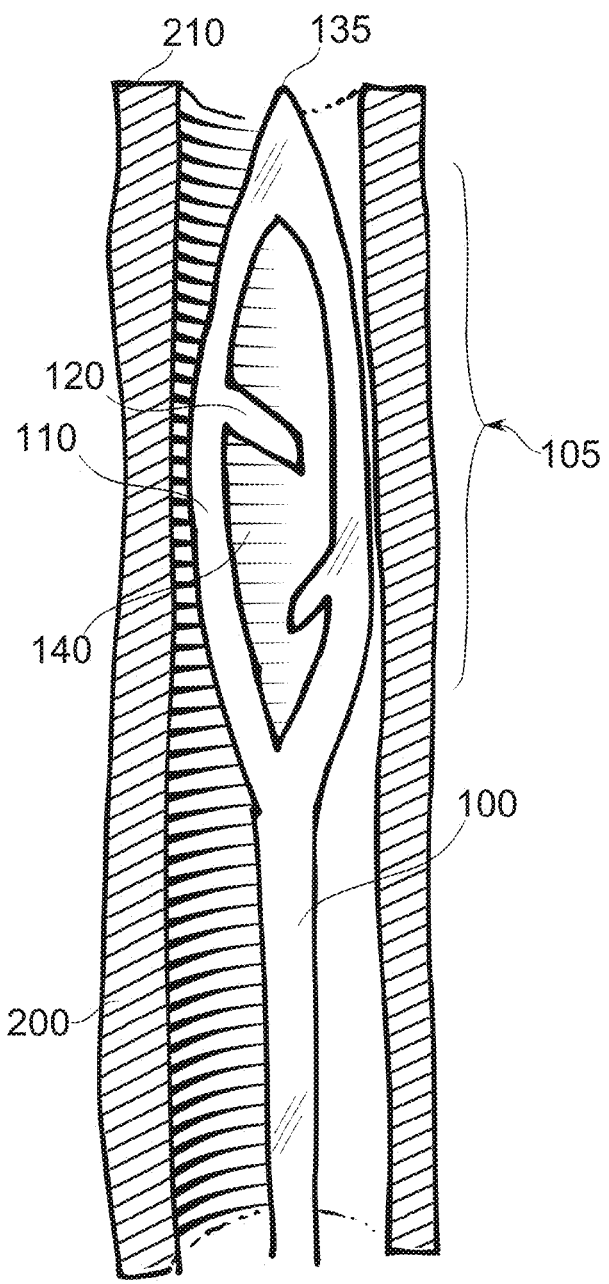
FIG. 1 is a simplified schematic of a biopsy needle held within a sheath and constrained to be in closed configuration, according to some exemplary embodiments of the present invention.

The present invention, in some embodiments thereof, relates to a device and method for collecting tissue samples, and, more particularly, but not exclusively, to biopsy needles introduced into the body within a sheath.

A tissue sampling apparatus and method are disclosed. Some embodiments comprise a biopsy needle having a laterally expandable distal portion comprising spines which move away from each other when unconstrained and which move towards each other when constrained to do so a sheath. Needles whose spines are moved away from each other (e.g. when unconstrained or when forced apart) are referred to herein as being in "open" configuration. Needles whose spines are close to each other, (e.g. when constrained to be so by a sheath) are referred to as being in "closed" configuration.

In some embodiments, needles have an expandable distal portion which comprises spines which support inward-pointing teeth designed to catch tissue samples when the needle is retracted from tissue.

In some embodiments, needles have an expandable distal portion which comprises spines supporting inward-pointing teeth designed to catch and hold tissue samples when the needle changes from open to closed configuration.

An optional method of use comprises providing a needle having spines which support inward-pointing teeth and which is held in a closed configuration by a sheath which contains the needle, advancing the sheath to near a sampling site, advancing the needle beyond the sheath to expand the expandable portion to an open configuration, retracting the needle into the sheath so that the expandable portion collapses and tissue samples are trapped among the teeth and spines, and removing the needle (and optionally also the sheath) so that tissue samples held therein may be garnered and examined.

Embodiments of the present invention provide potential advantages over prior art tissue sampling devices. Included among these advantages are the fact that the openable/closeable configurations of the expandable distal portion of the needle is better able than non-closeable configurations to limit and/or prevent contact between tissues samples being captured and other tissues of the body, because once the needle is in closed configuration the tissues are partially or completely enclosed in the construction of spines and teeth, and is subsequently further protected by subsequently being enclosed in the sheath before being extracted from the body, thereby limiting and/or preventing contact between potentially malignant and/or infected tissue and portions of the body along the path through which the needle is inserted into the body.

Additionally, the openable/closeable configurations of the expandable distal portion is more appropriate than a permanently open configuration for containing tissues which are soft and easily torn or distorted or dispersed, for example soft tissues of the lung, pancreas, and prostate. In some embodiments spines and can come together to form a closed configuration capable of capturing and transporting tissue samples which (once torn from their position in the body) are almost liquid in consistency, for example lung tissue.

In some exemplary embodiments of the invention, the sheath inner surface is shaped and/or processed in a manner which enhances and/or impedes movement of the needle therein. In one example, the sheath inner surface includes protrusions which space the needle from the majority of the surface of the walls of the lumen, possibly reducing stiction and/or preventing or reducing deformation of the needle. In some exemplary embodiments of the invention, the protrusions contact the wide side of the needle (e.g., for flat or ellipsoid-like needles). Optionally or alternatively, one or more protrusions are arranged to contact a thin side of the needle. Optionally, protrusions are provided for round needles, in which case they may be, depending on the embodiment, at various locations in a circumference of the lumen which carries the needle.

In some exemplary embodiments of the invention, the protrusion location is arranged with respect to an exit from the sheath and/or a desired exit direction of the needle, for example, serving to aim the needle.

An aspect of the invention relates to a catheter lead for pushing a needle to remote locations within the body. In some embodiments, the needle is built of one piece, with a base end long enough to reach a target region, for example, a part of the body to be biopsied. In some embodiments, the portion of the needle comprising the expandable region is attached to a catheter lead of sufficient length and appropriate rigidity to push a needle to a target region. The lead length, in some embodiments, is, for example: 10-20 cm, 15-40 cm, 30-50 cm, 40-70 cm, or another range of lengths having the same, larger, smaller, and/or intermediate bounds.

Before explaining at least one embodiment of the invention in detail, it is to be understood that the invention is not necessarily limited in its application to the details of construction and the arrangement of the components and/or methods set forth in the following description and/or illustrated in the drawings and/or given in the Examples. The invention is capable of other embodiments or of being practiced or carried out in various ways.

Overview

Figure 2:
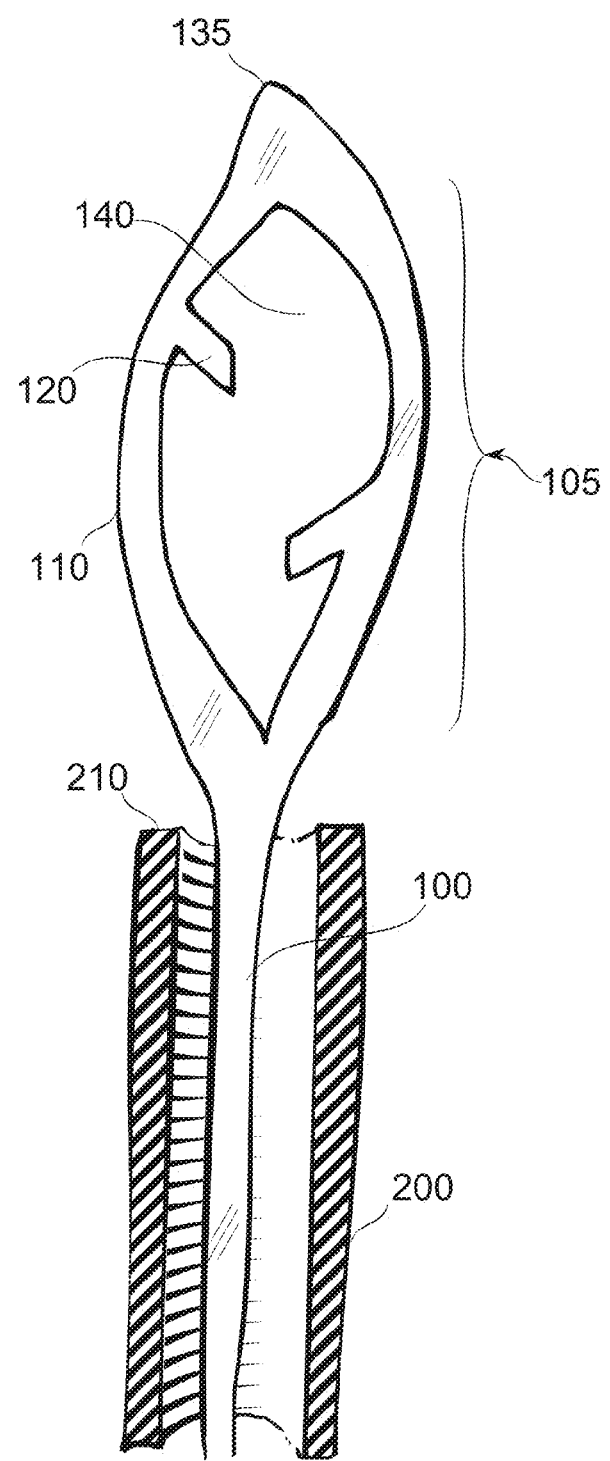
FIG. 2 is a simplified schematic of a biopsy needle extending beyond a distal portion of a sheath, and expanded to open configuration, according to some exemplary embodiments of the present invention.
Figure 3A:
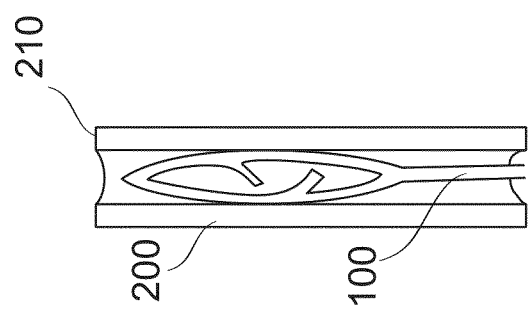
FIGS. 3A-3D are simplified illustrations of a method of sampling tissues, according to some exemplary embodiments of the present invention.
Figure 3B:
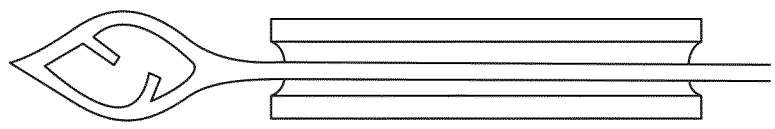
Figure 3C:
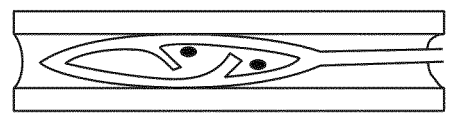
Figure 3D:
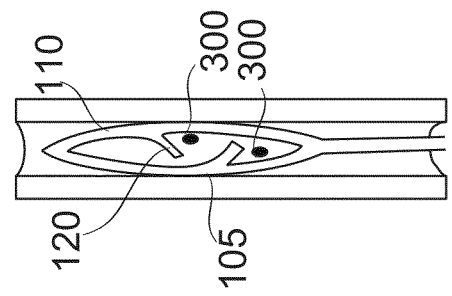

Referring now to the drawings, attention is drawn to FIGS. 1 and 2 which are simplified schematics of an apparatus comprising a biopsy needle held within a sheath, according to some exemplary embodiments of the present invention. FIG. 1 shows a needle 100 in closed configuration. FIG. 2 shows that needle in open configuration.

The present invention, in at least some embodiments thereof, comprises tissue sampling devices (referred to as "biopsy needles 100" or "needles 100" herein) which having a distal portion (called "laterally expandable portion 105" or "expandable portion 105" herein) which comprises a plurality of longitudinal elements (called "spines 110" herein), which spines are laterally expandable or moveable away from each other. A needle 100 whose spines are laterally distanced from each other is said to be in "open" configuration, as shown in FIG. 2. A needle 10 whose spines are positioned near each other is said to be in "closed" configuration, as shown in FIG. 1. According to the specific embodiment, lateral distancing is symmetrical or asymmetrical, and occurs in any lateral direction.

In some embodiments spines 110 comprise what we will refer to as "teeth 120". Teeth 120 are similar in purpose and may be similar in form to "notches 16" and "recesses 16" as described in PCT '080: they are any structural elements which serve to catch and/or cut and/or tear and/or capture portions of tissue, which may then be extracted from a body and subjected to pathological or other examinations.

In some embodiments teeth 120 are designed to be active in catching/cutting/tearing and/or otherwise capturing tissue particularly when needle 100 is being withdraw from tissue into which it has been inserted. Teeth so designed are shown in various figures discussed in detail below, but it is noted that the invention is not limited to this construction and that teeth in any orientation are contemplated.

In some embodiments, teeth 120 are positioned and/or oriented to point generally towards the interior of needle 100. Such positions and orientations may be compared to the positions and orientations of notches 16 of PCT '080: in that application notches 16 are shown in the figures to be positioned on outer surfaces of blade 10 and oriented to face outwards (i.e. away from the central axis of blade 10). In some embodiments of the present invention at least some of spines 110 present relatively smooth outer surfaces, and support teeth 120 pointing at least roughly inwards, i.e. towards (or nearly towards) a central longitudinal axis of needle 100 and/or towards other spines or teeth of needle 100 and/or towards an inner space 140 bordered by the spines and teeth. Teeth so oriented are referred to as "inward-pointing teeth", herein.

In some embodiments, an open configuration is assumed by lateral distancing of spines 110 within a plane chosen for descriptive purposes, for example a plane common to a flat side of a flat needle. Potentially, the transition to a closed configuration is compressive (pincer-like). In some embodiments, an open configuration is assumed by lateral distancing of spines which moves at least one spine out of the chosen plane. Potentially, the transition to a closed configuration is shearing (scissors-like). In some embodiments, distancing combines both motions. If more than one spine moves, movement it may be to the same or to opposite sides, and to an equal or differential extent. Characterizations such as compressive, shearing, pincer-like and scissors-like are illustrative; the actual forces applied depend on specifics of the embodiment such as the placement and orientation of the teeth 120.

In some embodiments spines 110 are designed to expand away from each other unless prevented from doing so, in a springy configuration. The Applicant has found nitinol to be a useful material for implementing embodiments of the invention, primarily because of its springiness and suppleness and ability to return to an original configuration when allowed to do so, but also optionally as influenced by nitinol's shape memory functionality. Other materials are also contemplated: stainless steel such as 'stainless-steel 1316L' and 'stainless steel 14-7PH' may for example be used, and implementations using other types of springy metal and/or springy plastic and/or other springy materials are contemplated.

Using a Sheath to Control Configuration of Biopsy Needle

In some embodiments needle 100 is inserted into a sheath 200 which constrains spines 110 to approach each other, putting needle 100 into "closed" configuration as shown in FIG. 1. According to optional methods of use disclosed in further detail below, closed needle 100 within sheath 200 is introduced into a body until it is contiguous to a region having tissues to be sampled. Then, according to some embodiments, expandable portion 105 is extended forward into body tissue and beyond a distal end 210 of sheath 200, which action frees expandable portion 105 to expand as shown in FIG. 2.

In some embodiments, when expandable portion 105 is extended beyond distal end 210 of sheath 200, expandable portion 105 expands, with spines 110 (each with its associated teeth 120) moving away from each other. Movement of spines 110 away from each other creates or expands what is called herein "inner space 140", roughly defined by spines 110 and teeth 120 as its outer boundary, as shown in the figures.

Expansion of needle 100 to its open configuration may facilitate contact between teeth 120 and body tissues to be sampled. When expandable portion 105 expands, some body tissue is likely to extend into an "interior space 140" of needle 100, since interior space 140 is expanded while spines 110 and teeth 120 move away from each other towards a position such as that shown in FIG. 2.

In some embodiments, for example in an exemplary embodiment shown in FIGS. 1 and 2, teeth 120 of needle 100 are oriented so as to 'hook' body tissue when needle 100 is withdrawn from body tissue into which it has been inserted. Teeth so oriented are termed "backward-pointing teeth" herein and in the claims below.

In some embodiments, retracting open needle 100 into sheath 200 and/or advancing sheath 200 over exposed expanded portions of needle 100 causes spines 110 and teeth 120 to approach each other, so that an effect whereby teeth 120 catch and hold body tissues is supplemented by an effect whereby captured tissue is trapped among spines 110 and teeth 120, where it is trapped within the (then greatly reduced) interior space 140 of needle 100 when needle 100 is in closed position. In some embodiments teeth 120 are shaped so as to cut off appropriately sized biopsy samples as spines 110 approach each other. Optionally, in some embodiments spines and/or teeth are shaped with cutting edges which cut off portions of tissue, which cut-off portions are subsequently entrapped by the spines and teeth, optionally when the needle is retracted from tissue and optionally when said needle changes from open to closed configuration.

Once needle 100 and its trapped body tissue material is enclosed in sheath 200 as shown in FIG. 1, needle 100 and/or needle 100 together with sheath 200 may easily be removed from the body. In some embodiments, sheath 200 and needle 100 are removed together. In some embodiments needle 100 may be extracted from sheath 200, leaving sheath 200 in place, e.g. to guide an additional needle 100 to a new position within a region of interest in the body and near the position of the previous needle 100.

In some embodiments body tissues trapped within needle 100 may be easily recovered (e.g. by a laboratory technician), since needle 100, which holds the tissues tightly while in sheath 100, opens itself, permitting a technician to access material in the needle's interior, once needle 100 is removed from a sheath 200 which constrained it to be closed.

As shown in an exemplary embodiment shown in FIGS. 1 and 2 and in other figures herein, teeth 120 are positioned and/or oriented so as to point generally towards the interior of needle 100. In some embodiments of the present invention at least some of spines 110 present relatively smooth outer surfaces, and support teeth 120 pointing at least roughly inwards, i.e. towards (or nearly towards) a central longitudinal axis of needle 120 and/or towards other spines or teeth of needle 100. Teeth so-oriented are referred to herein and in the claims below as "inward-pointing teeth".

Optionally, leading edge 135 of needle 100 is sharp so as to facilitate advancing needle 100 into body tissue. Leading edge 135 may also be a relatively flat surface, which may facilitate keeping needle 100 in a same plane as it advances into tissue.

Method for Taking Tissue Samples

Attention is now drawn to FIG. 3, which is an illustration of a method for sampling body tissues, according to some exemplary embodiments of the present invention.

FIG. 3 shows four stages in a sampling process. At 'A' a needle 100 is shown in closed configuration within a sheath 200. The sheath/needle combination is assumed to have been advanced to a vicinity from which a surgeon wishes to remove a biopsy sample.

(Note that sheath 200 containing needle 100 can be inserted into a body, e.g. through a body conduit or through a trocar or by other means. In some embodiments distal end 210 of sheath 200 may itself be a sharp distal end capable of puncturing body tissue. However, in some alternative embodiments sheath 200 may simply be placed outside a body and contiguous to it at a position from which a surgeon wishes to take tissue samples from a body portion near the skin).

At 'B' needle 100 is shown to be advanced beyond distal end 210 of sheath 200, and in open configuration.

At 'C', needle 100 is withdrawn back into sheath 200, bringing with it tissue samples 300 caught by teeth 120 and/or spines 110. In some embodiments (not shown in this figure) teeth 120 are oriented to catch and/or hold tissue as needle 100 advances. In some embodiments (such as in an exemplary embodiment shown in the figure) teeth 120 are oriented so as to catch and/or hold tissue as needle 100 is retracted from body tissues into which it had advanced. In some embodiments, teeth 120 and/or other portions of spines 110 are sharpened and/or oriented in such a way as to catch and/or hold body tissue as expandable portion 105 contracts, as it does when needle 100 changes from an open to a closed configuration, which may happen as needle 100 is pulled back into sheath 200 as shown at 'C'.

Once needle 100 is retracted into sheath 200, the combined sheath and needle may be easily removed from the body, as shown at 'D'.

Figure 4:
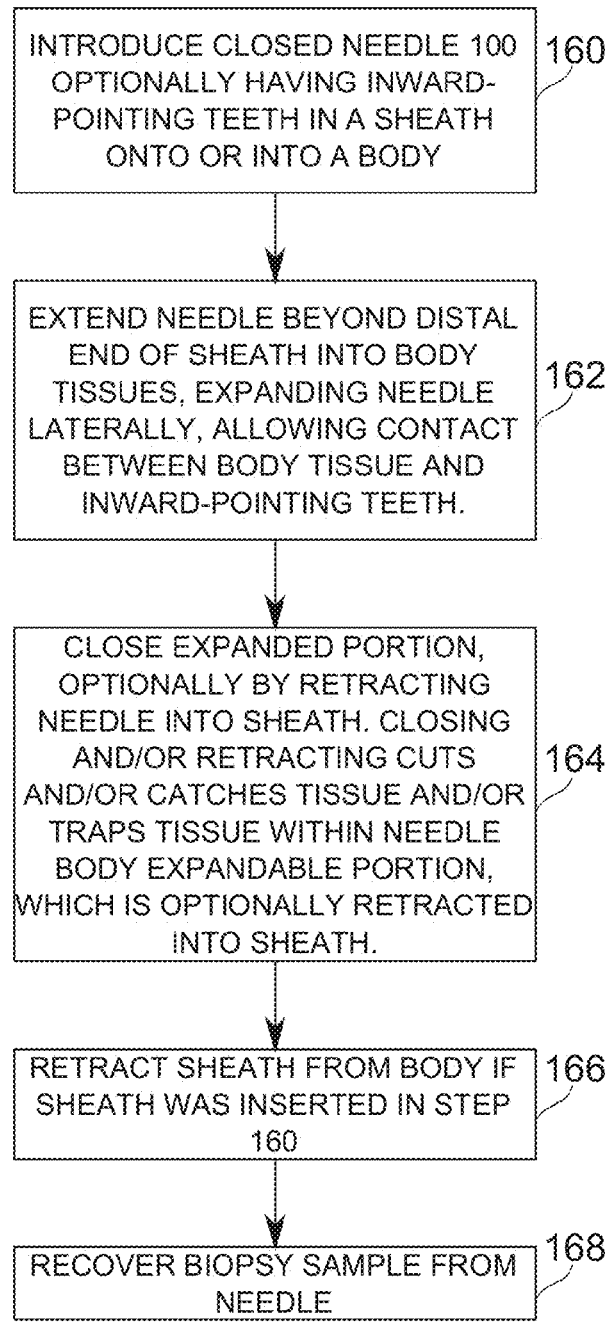
FIG. 4 is a simplified flow chart presenting the method illustrated in FIG. 3, according to some exemplary embodiments of the present invention.
Figure 5D:
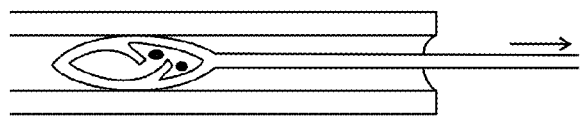
FIGS. 5A-5D are simplified illustrations of an additional method of sampling tissues, according to some exemplary embodiments of the present invention.
Figure 5C:
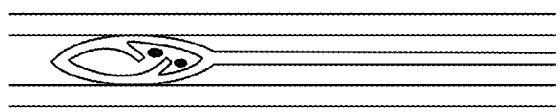
Figure 5B:
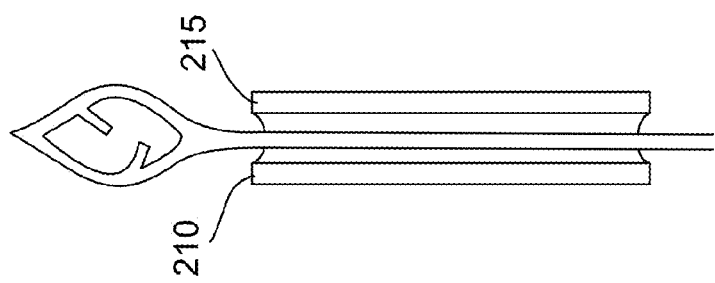
Figure 5A:
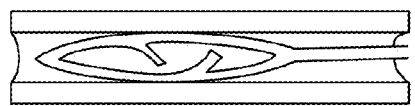

Attention is now drawn to FIG. 4, which is a simplified flowchart of a process illustrated by FIG. 3, according to some exemplary embodiments of the present invention.

At 160, a needle 100 in closed configuration and contained within a sheath 200 is introduced into a body. (As mentioned elsewhere, in an alternative embodiment sheath 200 may optionally remain external to the body.) The expression "inward-pointing teeth" used in portion 160 of FIG. 4 refers to the fact, described above, that in some embodiments teeth 120 are held by or connected to spines 110, spines 110 present a smooth or relatively smooth external surface able to slide along body tissues and/or along inside surfaces of sheath 200 with little resistance, and teeth 120 supported by and/or attached to and/or comprised within spines 110 are oriented not towards tissues outside needle 100 but rather point towards other spines and/or teeth or toward a portion of inner space 140.

At 162, needle 100 is pushed forward within sheath 200 until at least a portion of expandable portion 105 extends beyond distal end 210 of sheath 200, so that expandable portion 105 of needle 100 expands laterally, enabling contact between body tissue and inward-pointing teeth 120.

At 164, needle 100 is retracted into sheath 200, during which process body tissues are trapped within needle 100. At 166 sheath 200, if it was inserted into the body at 160, is removed from the body together with needle 100. (Optionally, needle 100 may be removed from sheath 200, leaving sheath 200 in place).

At 168, tissue samples trapped within needle 100 may be removed and subjected to pathology or other examinations.

Alternative Method of Tissue Sampling

Attention is now drawn to FIG. 5, which is an illustration of an alternative process of tissue sampling, according to some exemplary embodiments of the present invention.

FIG. 5 shows four stages in a sampling process. At 'A' a needle 100 is shown in closed configuration within a sheath 200. The sheath/needle combination is assumed to have been advanced to a vicinity from which a surgeon wishes to remove a biopsy sample.

At 'B' needle 100 is shown to be advanced beyond distal end 210 of sheath 200, and to be in open configuration.

At 'C' in FIG. 5, in this alternative embodiment sheath 200 is advanced, closing needle 100, and at 'D', needle and (optionally) sheath 200 are withdrawn from the body. Note that the method at 'C' is in contrast to that shown in FIG. 3, wherein needle 100 was retracted rather than sheath 200 being advanced. In practice, these movement alternatives may be combined according to the convenience of a surgeon and the specifics of the patient and the sampling process, and according to the type of sheath used. In some embodiments sheath 200 is provided with a cutting edge 215 which cuts off tissue extending towards or into inner space 140, thereby facilitating capture.

It is also noted that advancing sheath 200 to force a needle 100 into a closed configuration does not necessarily require that sheath 200 be advanced to completely cover an exposed distal portion of a needle 100 in open configuration. FIG. 9C, discussed in further detail below, shows two arrows labeled 198 and 199. It may be appreciated that advancing a close-fitting sheath 200 from approximately the position of arrow 198 to approximately the position of arrow 199 would result in substantially closing the open portion of the needle 100 shown in that figure, even though only a small portion of the laterally expandable distal portion 105 would be covered by sheath 200 at that point.

It is to be noted that in some embodiments (not shown in this figure) teeth 120 are oriented to catch and/or hold tissue as needle 100 advances, in some embodiments (such as in an exemplary embodiment shown in FIG. 5) teeth 120 are oriented so as to catch and/or hold tissue as needle 100 is retracted from body tissues into which it had advanced, and in some embodiments, teeth 120 and/or other portions of spines 110 may be sharpened and/or oriented in such a way as to catch and/or hold body tissue as expandable portion 105 contracts, as it does when needle 100 changes from an open to a closed configuration, which may happen as needle 100 is pulled back into sheath 200 as shown at 'C' of FIG. 3 and/or when sheath 200 is extended over distal portions of needle 100 as shown at 'C' of FIG. 5.

Figure 6:
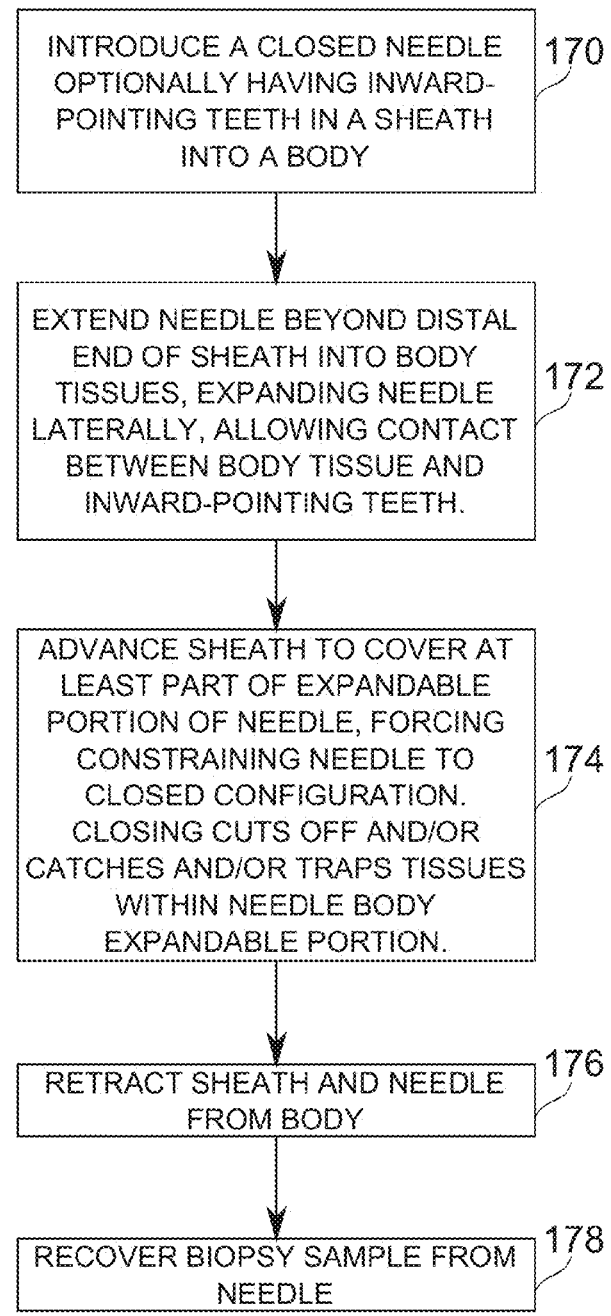
FIG. 6 is a simplified flow chart presenting the method illustrated in FIG. 5, according to some exemplary embodiments of the present invention.

Attention is now drawn to FIG. 6, which is a simplified flowchart of a process illustrated by FIG. 5, according to some exemplary embodiments of the present invention.

At 170, a needle 100 in closed configuration and contained within a sheath 200 is introduced into a body.

At 172, needle 100 is pushed forward within sheath 200 until at least a portion of expandable portion 105 extends beyond distal end 210 of sheath 200, so that expandable portion 105 of needle 100 expands laterally, enabling contact between body tissue and inward-pointing teeth 120.

At 174, sheath 200 is advanced so as to cover expandable portion 105 of needle 100, thereby forcing needle 100 into closed configuration by applying contracting lateral pressures on spines 120 of needle 110. Tissue samples are thereby trapped within needle 100, where they may be retracted from the body at 176 and retrieved for analysis at 178.

Exemplary Flat Biopsy Needles

Figure 7:
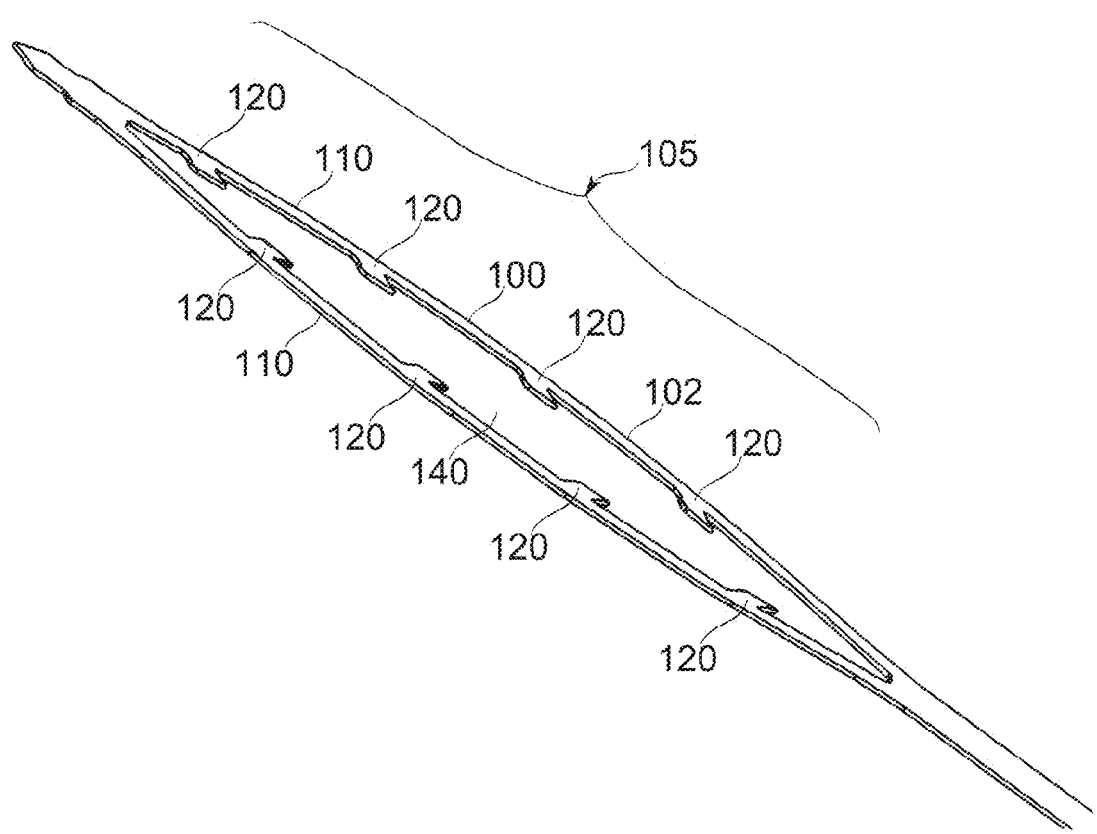
FIGS. 7 and 8 are views of flat biopsy needles, according to some exemplary embodiments of the present invention.
Figure 8:
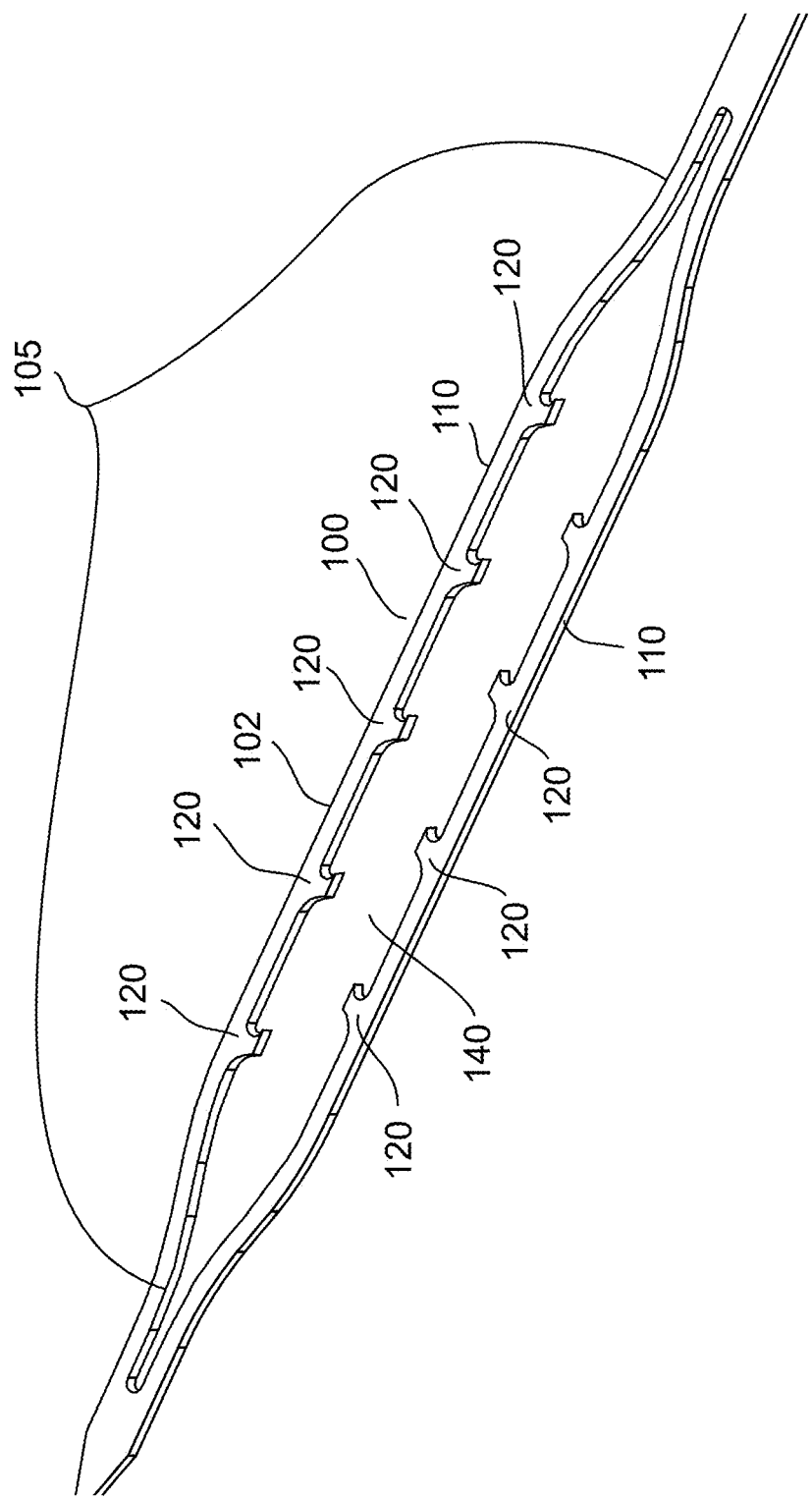

Attention is now drawn to FIGS. 7 and 8, which are simplified views of relatively 'flat' biopsy needles 100, according to some exemplary embodiments of the present invention.

Needles 100 with 'flat' configuration are labeled 102 in the Figures. Of course, needles 102 are not actually flat in the sense of being two-dimensional, but they are relatively thin in one dimension, and can expand and contract, optionally in a dimension perpendicular to the dimension in which they are thin. In some embodiments, at least distal portions of needles 102 are designed to be bendable, and may be used to thrust laterally from a sheath or introducer, as taught in detail in PCT '080 and discussed with reference to FIG. 9D, below. These embodiments may be implemented using a sheath which comprises an elongated sheath body having an interior lumen with an arcuate slot forming a continuum between the interior lumen and an exterior aperture at the end thereof, wherein the exterior aperture is disposed laterally (i.e. not longitudinally) on the sheath body and the cross section of the arcuate slot generally corresponds in shape to the longitudinal profile of the needle, as taught in PCT '080. Construction of such an arcuate slot in a sheath head is shown in FIG. 9D, discussed below.

As may be seen by comparing FIGS. 7 and 8, needles 102 may be presented in a variety of shapes and configurations, with specific features such as the shape of spines 110 and/or of teeth 120, numbers of teeth 120, and other design considerations being determined as appropriate and convenient for any specific sampling task, since different feature configurations will be appropriate for differing tissue sampling sites, different tissues, and differing surgeons' techniques.

Figure 9A:
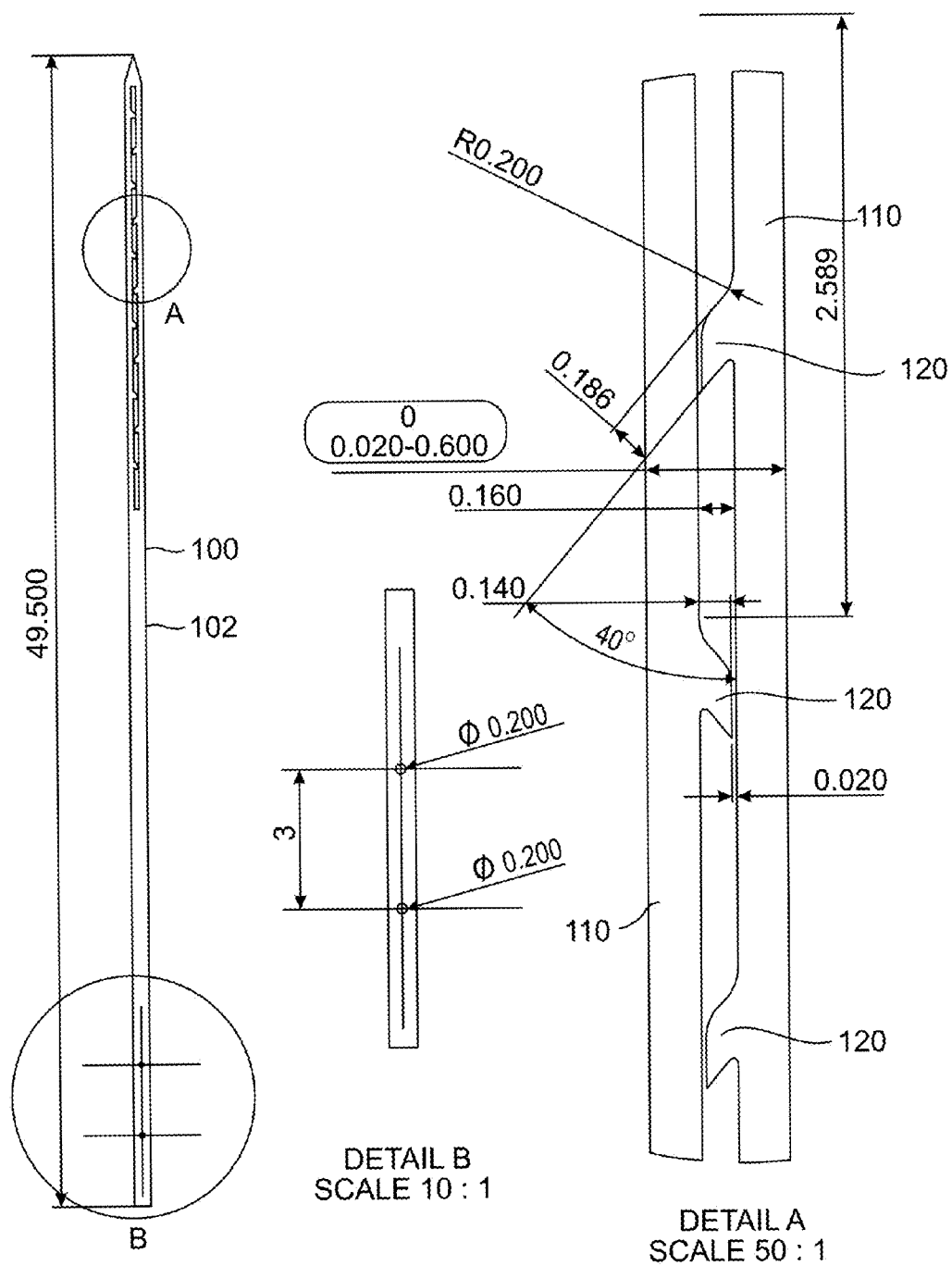
FIG. 9A is a detailed view of a biopsy needle in closed configuration, showing exemplary dimensions and detailed images of several portions of the needle, including inward-pointing teeth, according to some exemplary embodiments of the present invention.

Attention is now drawn to FIG. 9A, which is a detailed view of a biopsy needle 100 (and 102) in closed configuration, according to some exemplary embodiments of the present invention. Portions of a needle 100 are highlighted by circles in the figure, and magnified views of those highlighted portions are shown in "detail A" and "detail B", which provide exemplary dimensions for an exemplary embodiment. However, it is to be understood that the specific design and dimensions presented in figures herein are exemplary only, and are not to be considered limiting.

Figure 9B:
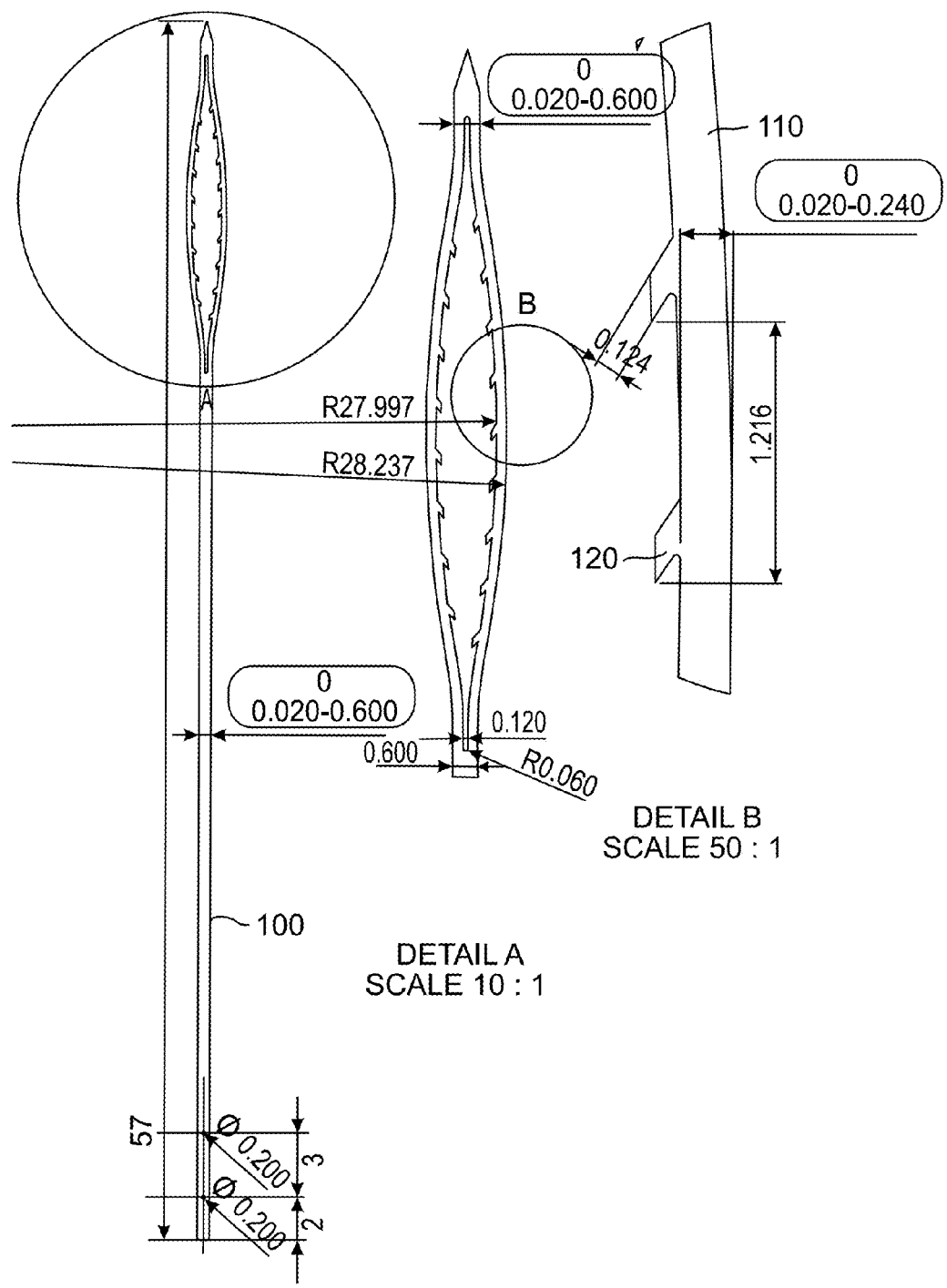
FIG. 9B is a detailed view of a biopsy needle in open configuration, showing exemplary dimensions and detailed images of several portions of the needle, including inward-pointing teeth, according to some exemplary embodiments of the present invention.
Figure 9C:
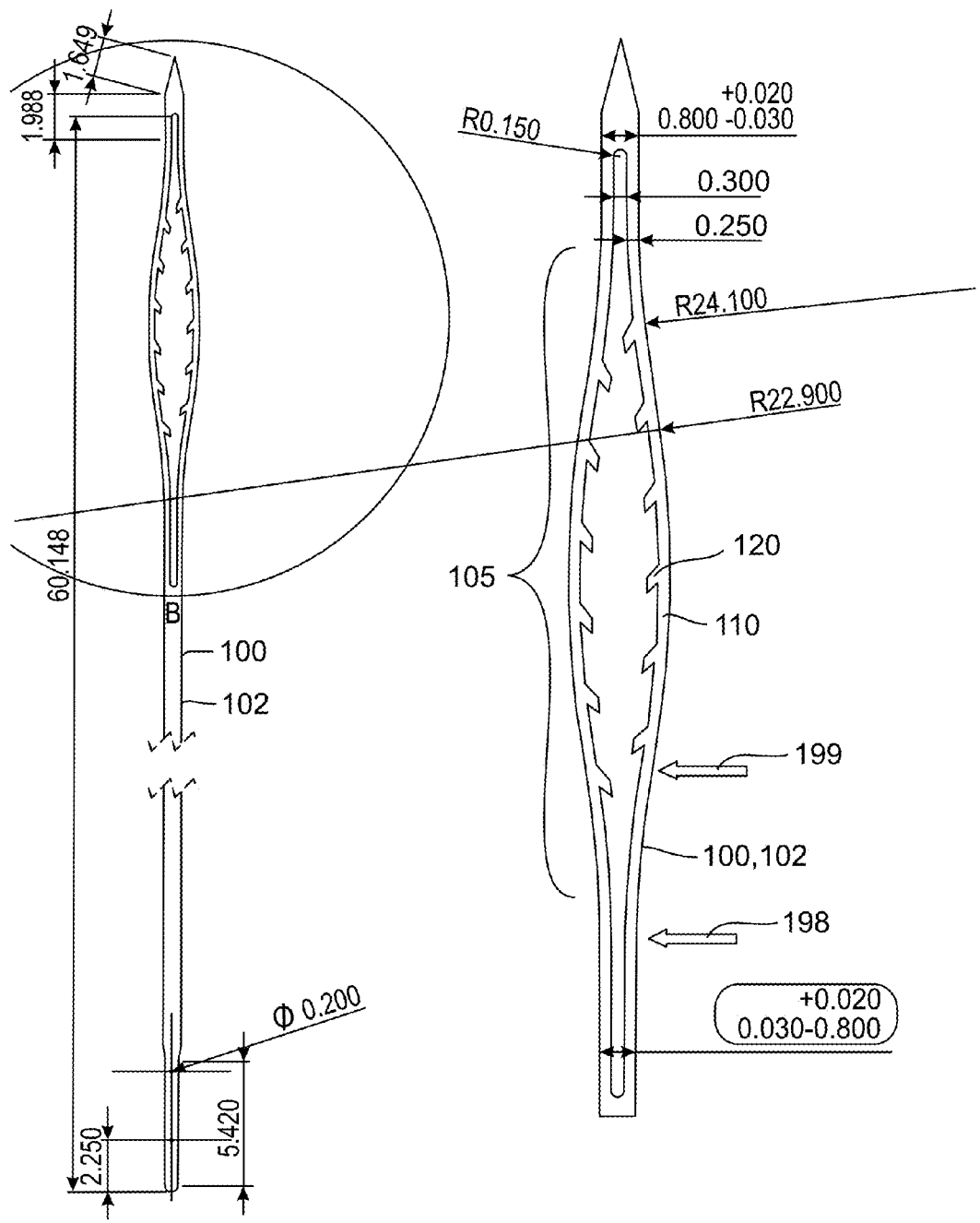
FIG. 9C is an additional detailed view of a biopsy needle in open configuration, showing exemplary dimensions and detailed images of several portions of the needle, according to some exemplary embodiments of the present invention.
Figure 9D:
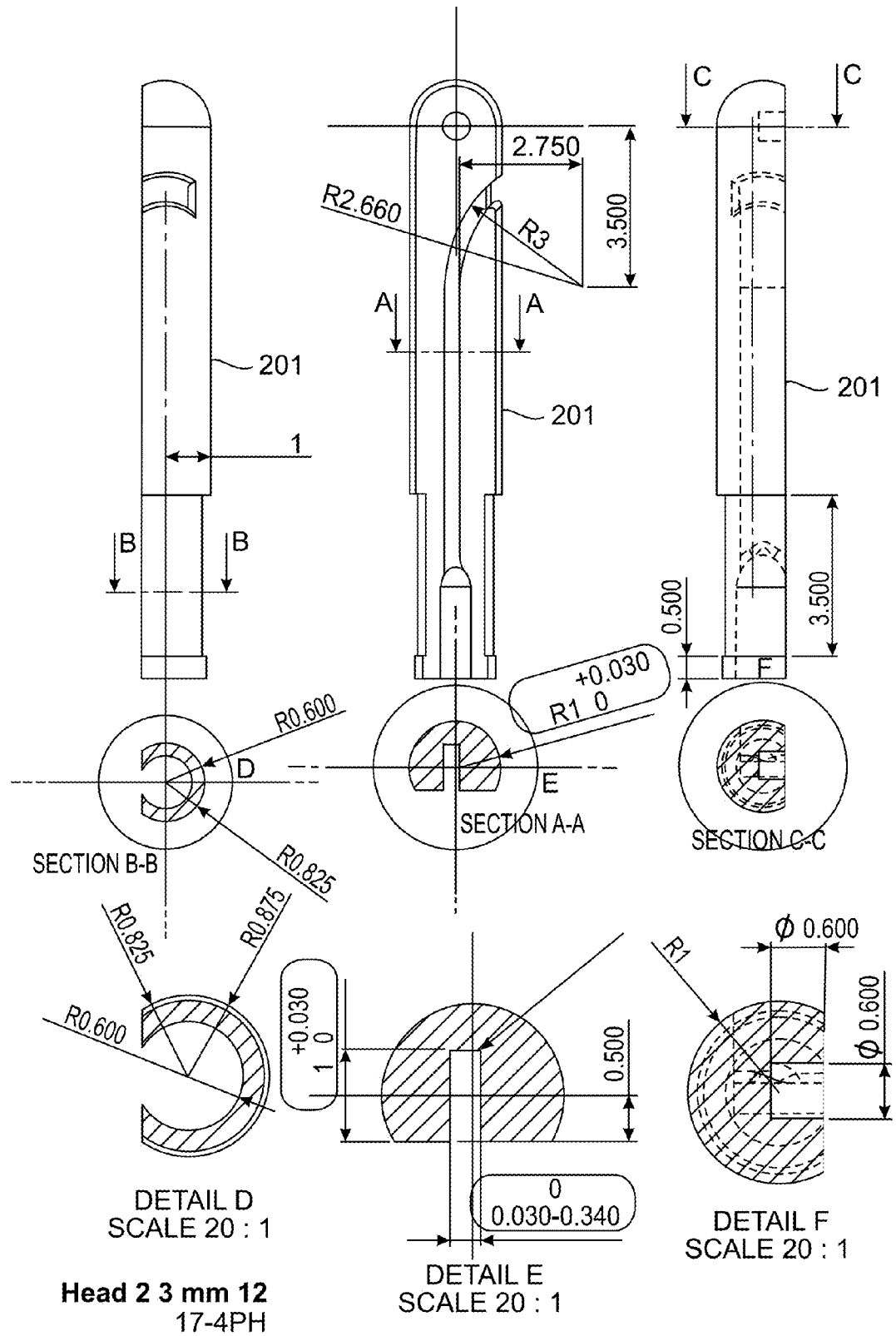
FIG. 9D is a detailed view of an exemplary sheath head usable with flat biopsy needles, according to some embodiments of the present invention.
Figure 9E:
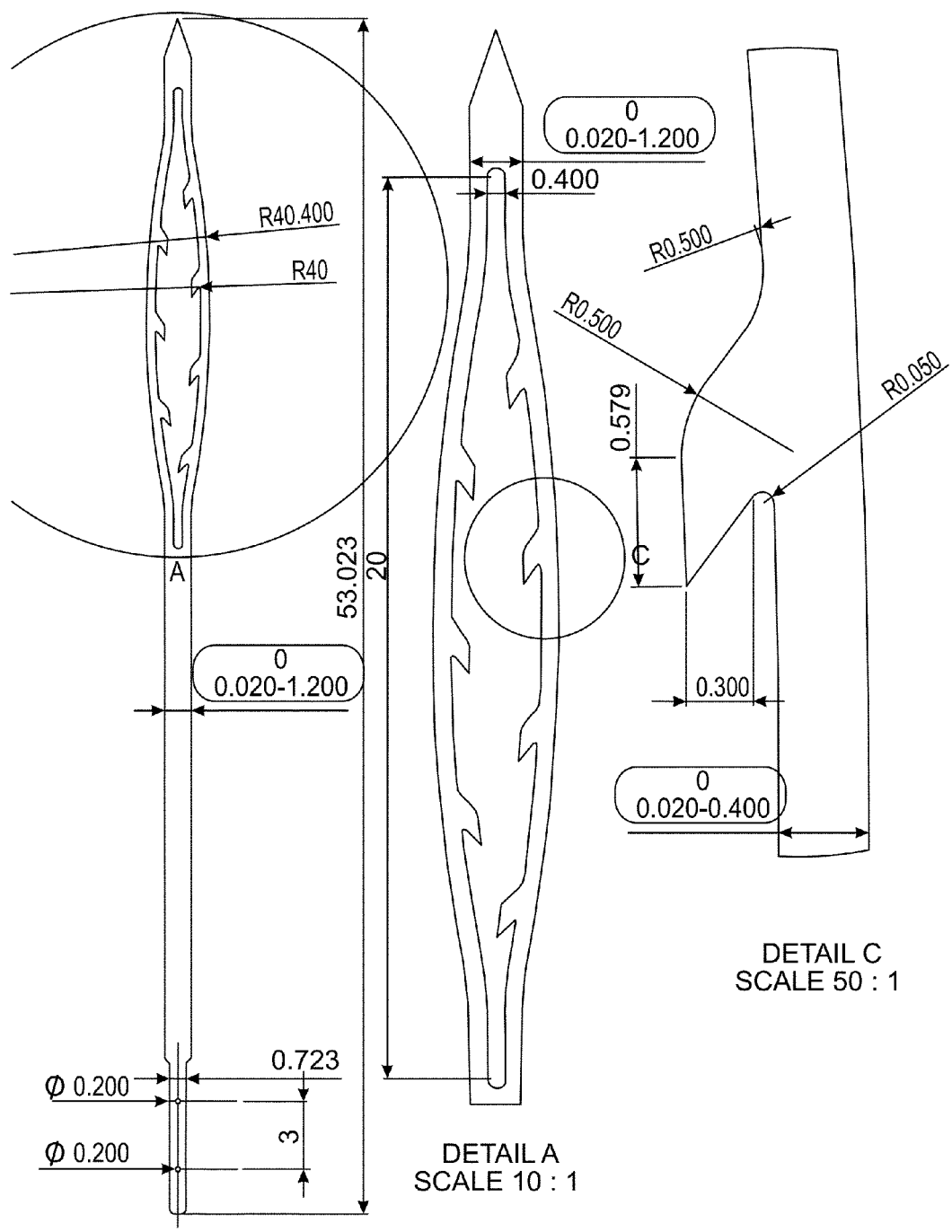
FIGS. 9E-9I are detailed views of embodiments providing dimensional information, according to some exemplary embodiments of the invention.
Figure 9F:
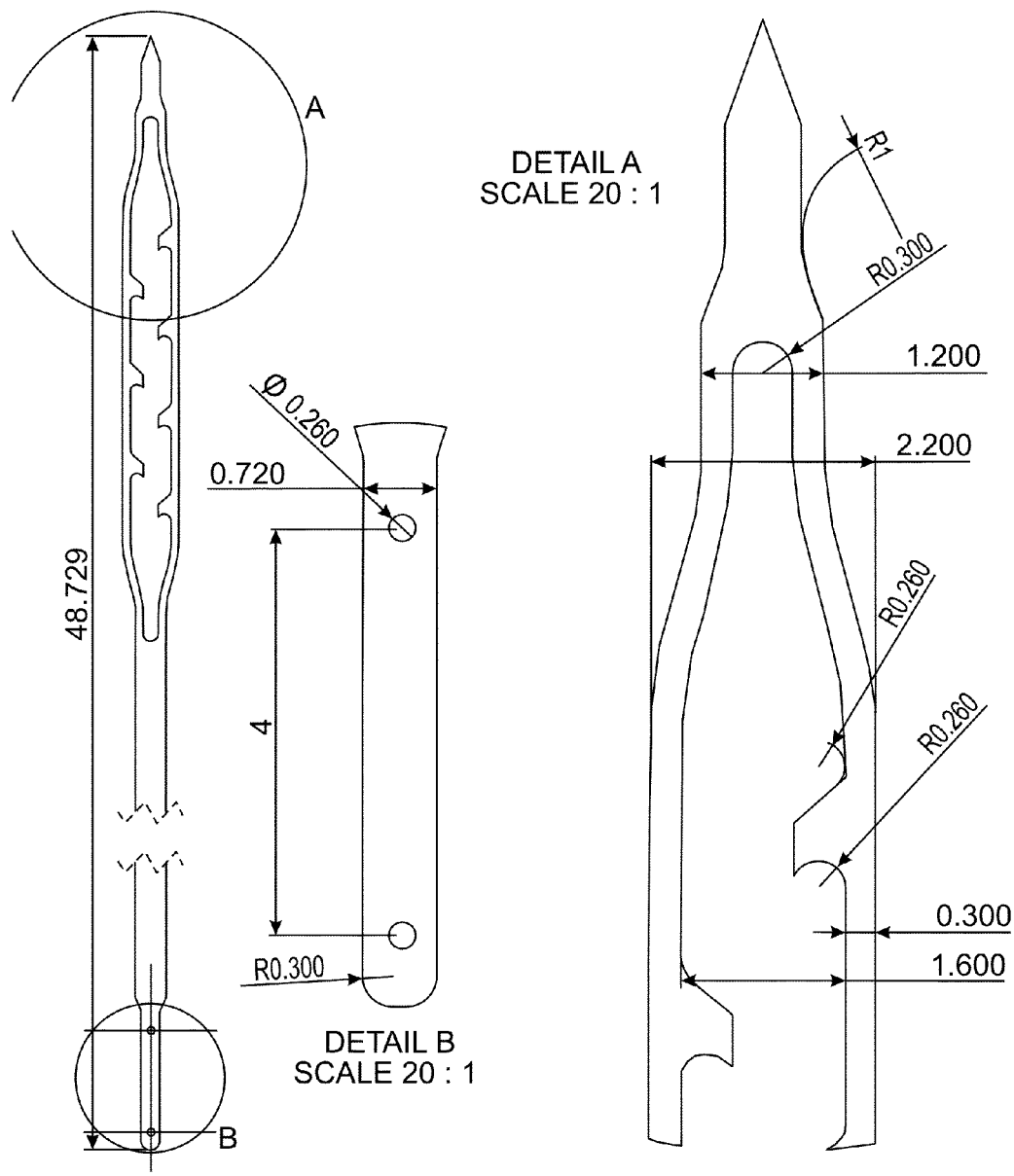
Figure 9G:
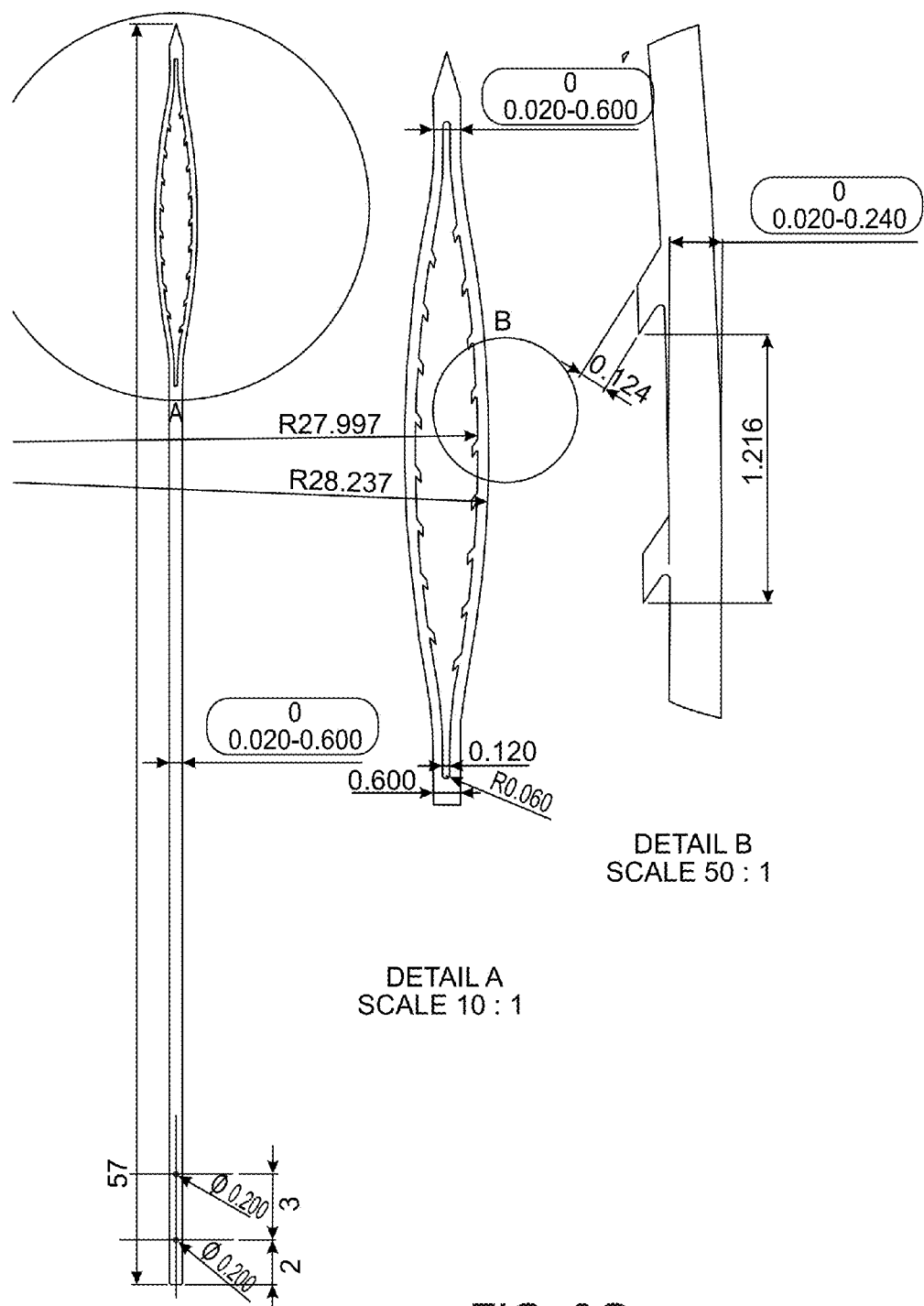
Figure 9H:
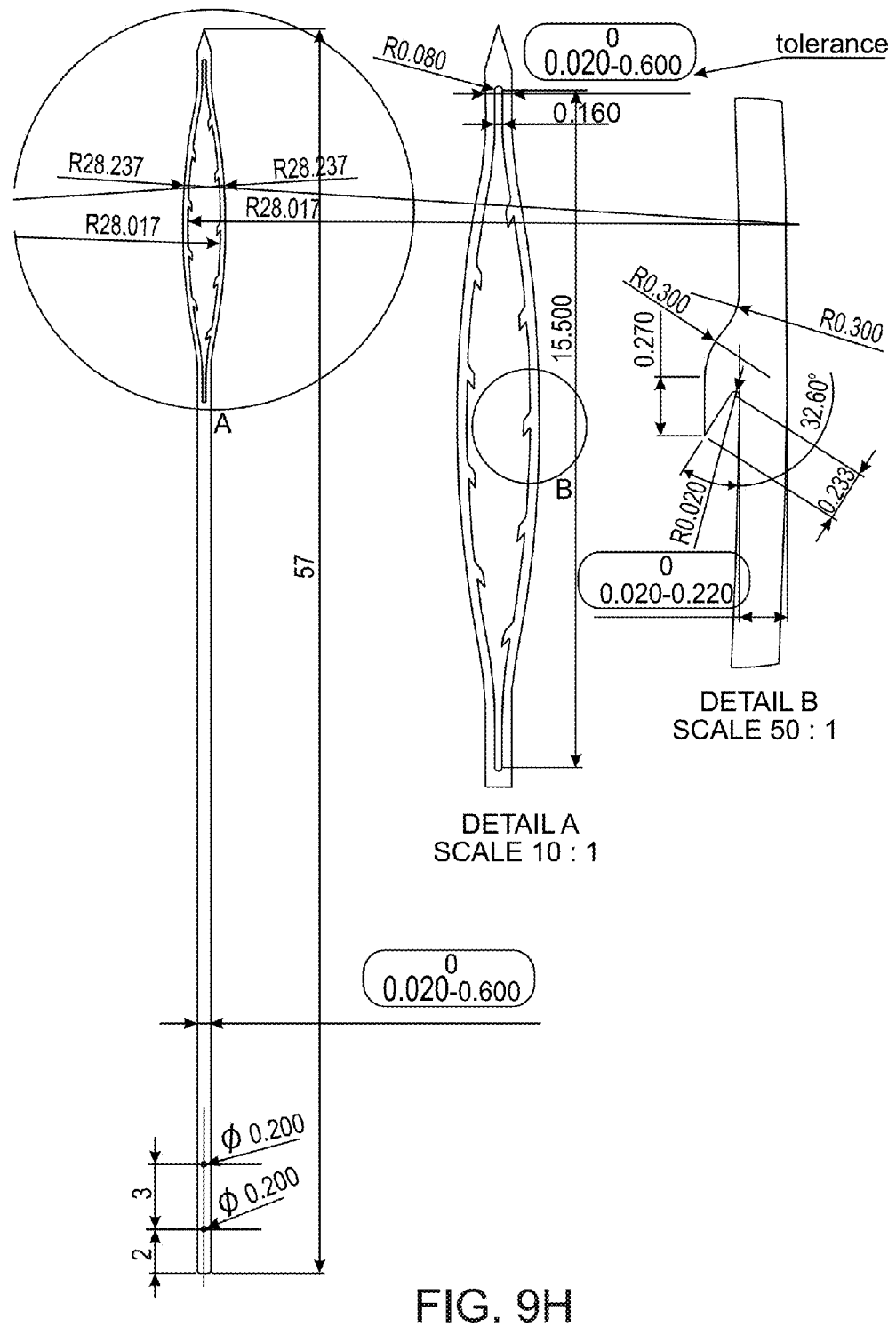

Attention is now drawn to FIG. 9B, which is a detailed view of the biopsy needle shown in FIG. 9A, with the difference that whereas FIG. 9A showed the needle in closed configuration, FIG. 9B shows the needle in open configuration. FIG. 9B also presents portions of needle 100 highlighted by circles, and magnified detail views of those highlighted portions labeled "detail A" and "detail B". Here too, exemplary (and non-limiting) dimensions are provided.

Attention is now drawn to FIG. 9C, which provides an additional detailed view of an embodiment of a flat biopsy needle, showing exemplary (and not limiting) dimensions and other details, according to some exemplary embodiments of the invention.

Attention is now drawn to FIG. 9D, which is a detailed view of an exemplary sheath head 201 usable to direct a flat needle 100 into a lateral direction for taking tissue samples. PCT '080, discussed in the background section above, teaches the use of a similarly shaped sheath head to direct a curvable biopsy blade into a tissue which is "off axis" with respect to the general direction of insertion of a biopsy apparatus. For example, a mechanism such as that described in PCT '080 may be used to advance a sheath along a body lumen (for example, a prostatic urethra), and at a desired location, a blade may be extended from a sheath head as shown in PCT '080 in a lateral direction (i.e. 'lateral' with respect to the general 'forward' direction of advancement of the sheath e.g. along a urethra), thereby enabling the taking of samples of tissues which are adjacent to (and not directly in front of) a path (e.g. along a body lumen such as a urethra) along which the sheath is advanced.

Figure 9I:
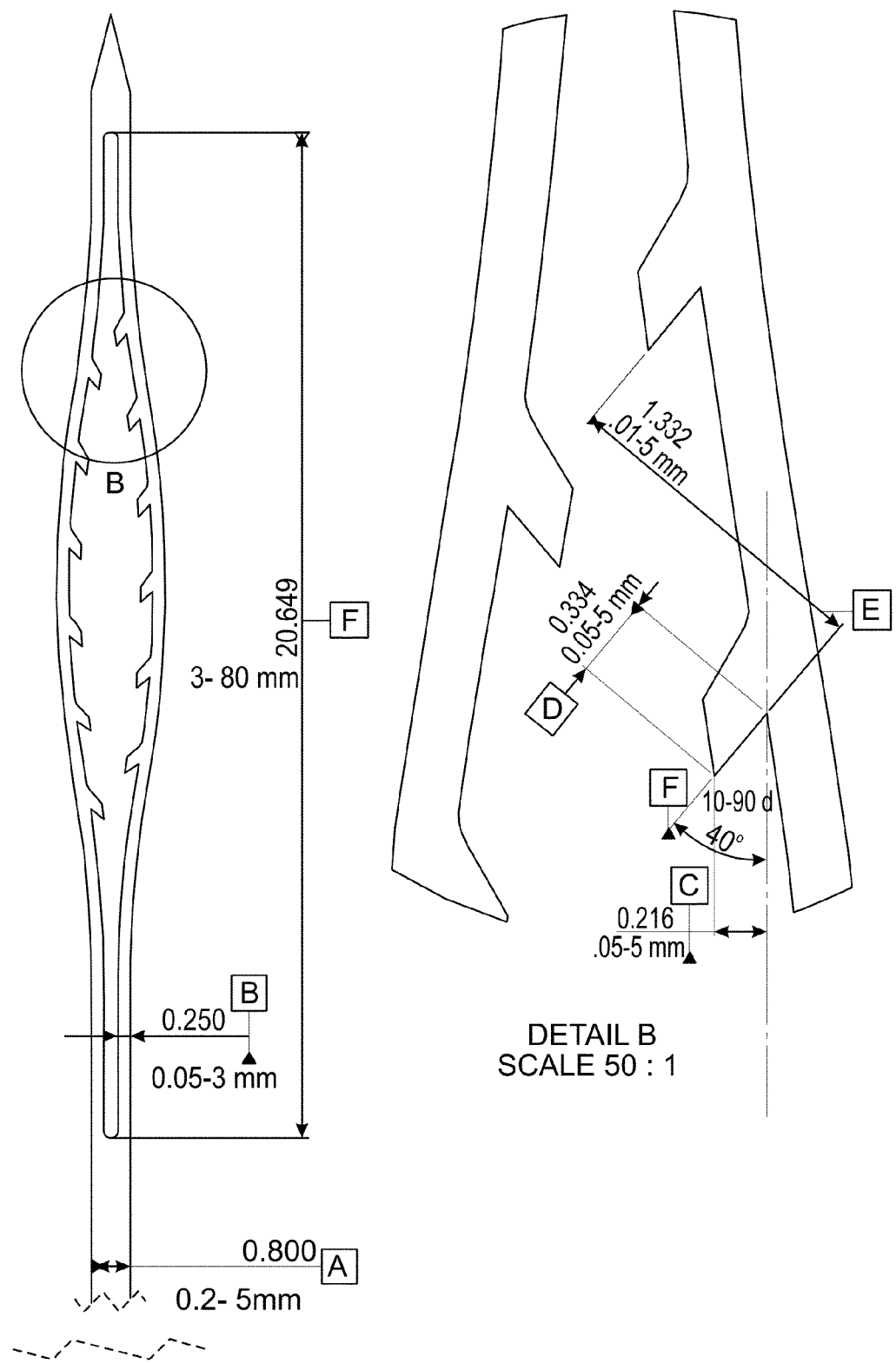
Figure 9J:
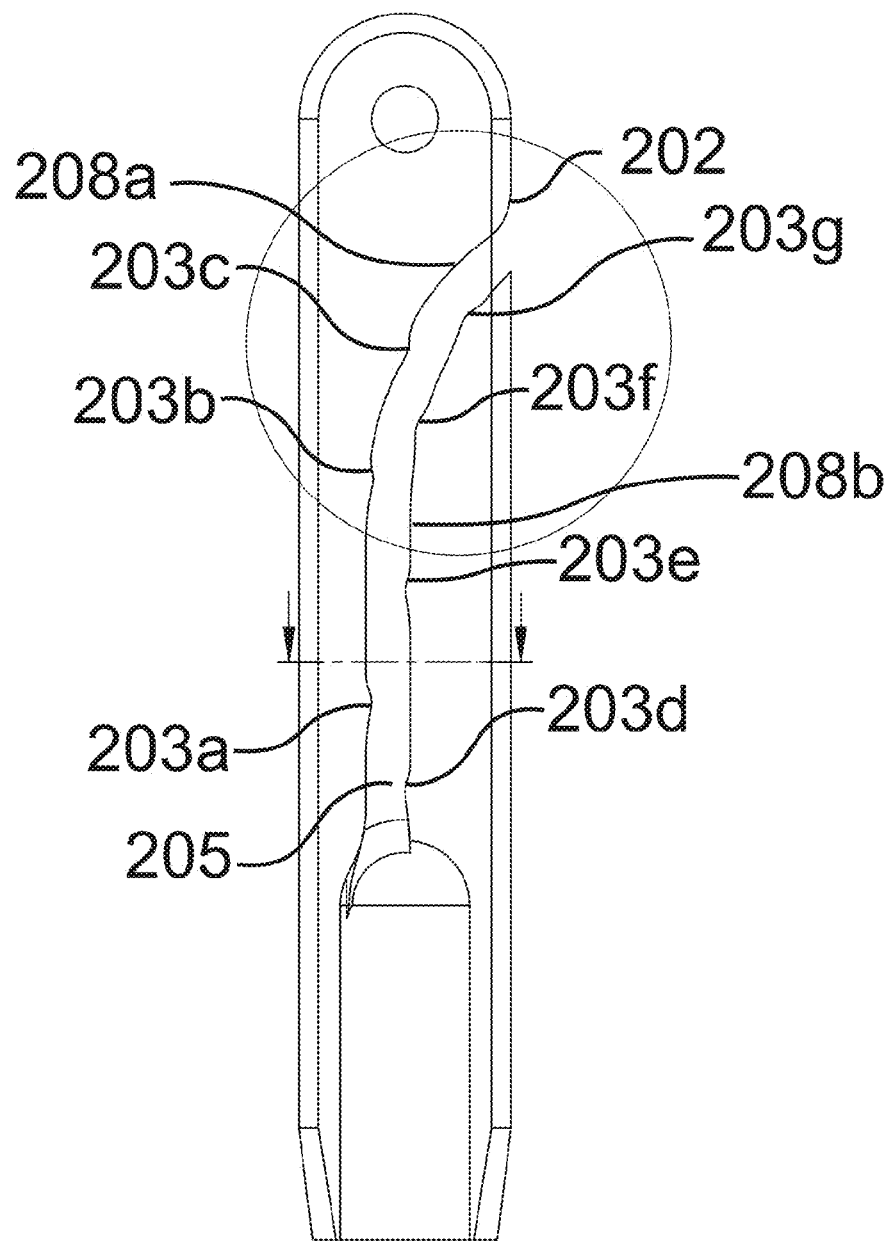
FIGS. 9J-9N are detailed views of an exemplary sheath head with a lumenal surface formed with protrusions sufficient to lift at least a portion of a flat biopsy needle away from impeding interactions with adjacent portions of said lumenal surface, according to some exemplary embodiments of the present invention.

Attention is now drawn to FIGS. 9J-9N which are detailed views of a sheath head 202 usable to direct a flat needle 100 into a lateral direction for taking tissue samples, according to some exemplary embodiments of the invention. FIG. 9J is an overall cut-away side view of a sheath head, according to some exemplary embodiments of the invention. It shows cross-sectional profiles of two opposite walls of a lumenal surface 208.

In some embodiments, and according to the embodiment of the invention and the portion of the lumen considered, the walls of the lumenal surface 208a and 208b are broadly straight or arcuate in their said profiles. However, said walls deviate in part from being strictly straight or arcuate in that they are formed with a plurality of distinct and distinguishable protrusions 203a-203g. In some embodiments of the invention, and according to the embodiment, said protrusions further distinguish the course of the actual lumenal surface from one or both of idealized straight or arcuate profiles which portions of the sheath lumen 205 approximate, by one or both of their recurrence and their more localized character.

Additionally or alternatively, in some embodiments of the invention, the heights of a plurality of said protrusions are sufficient to separate at least a portion of said needle 100 from potentially impeding interactions with adjacent portions of said lumenal surface, for example as may be due to actual sliding motion, or upon the application of force tending to produce a sliding motion. In some embodiments of the invention, said heights furthermore do not protrude into the sheath lumen so much that they themselves constitute a fully, more-than-fully, or largely counteracting impediment to said motion or application of force, when suitably shaped and arranged. In some embodiments, said protrusions impose themselves 0.05-0.06 mm into the sheath lumen. In other embodiments, the protrusions act (e.g., are shaped, sized and/or arranged) to resist and/or regulate the forward and/or reverse movement of the needle and/or affect its in-sheath opening and closing.

Figure 9K:
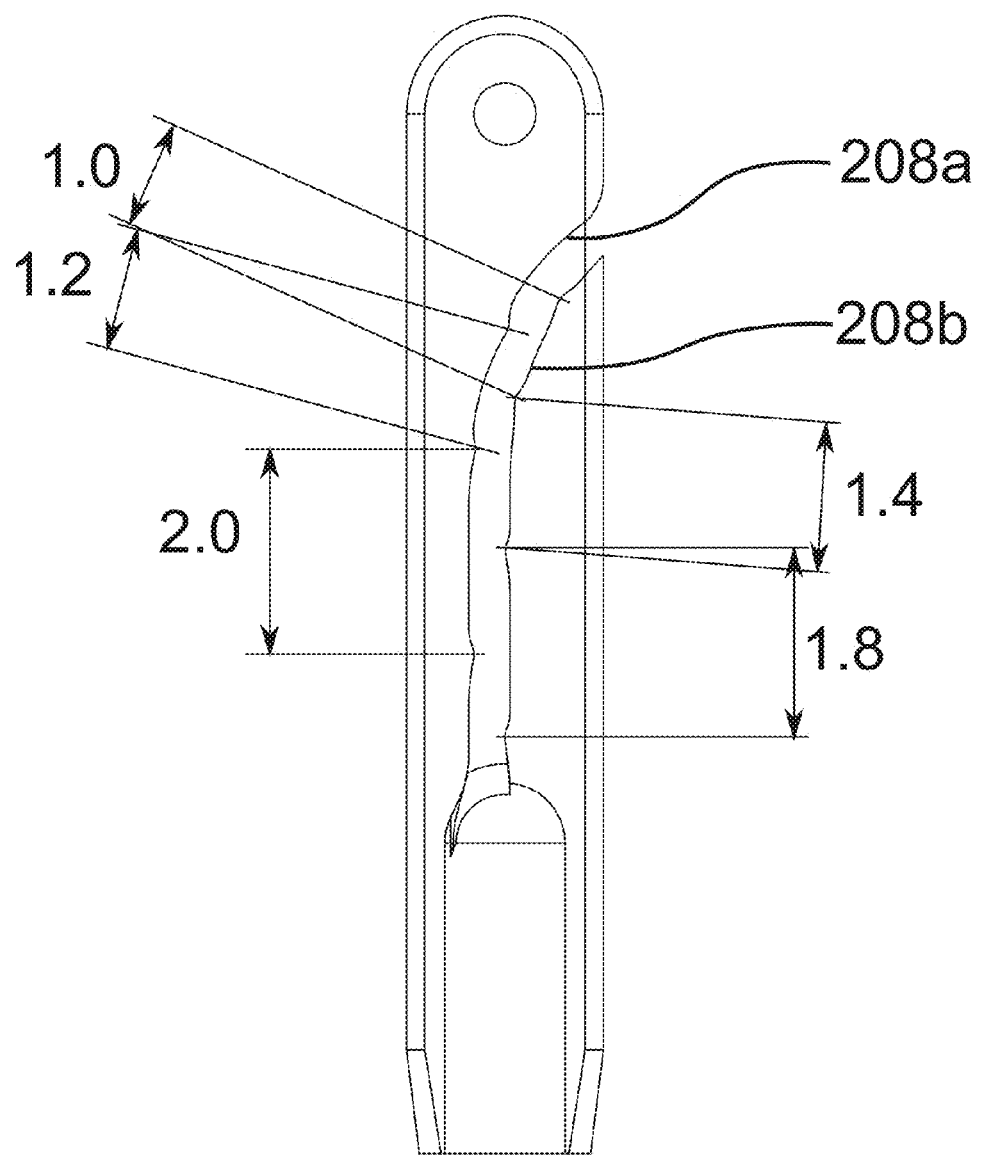
Figure 9L:
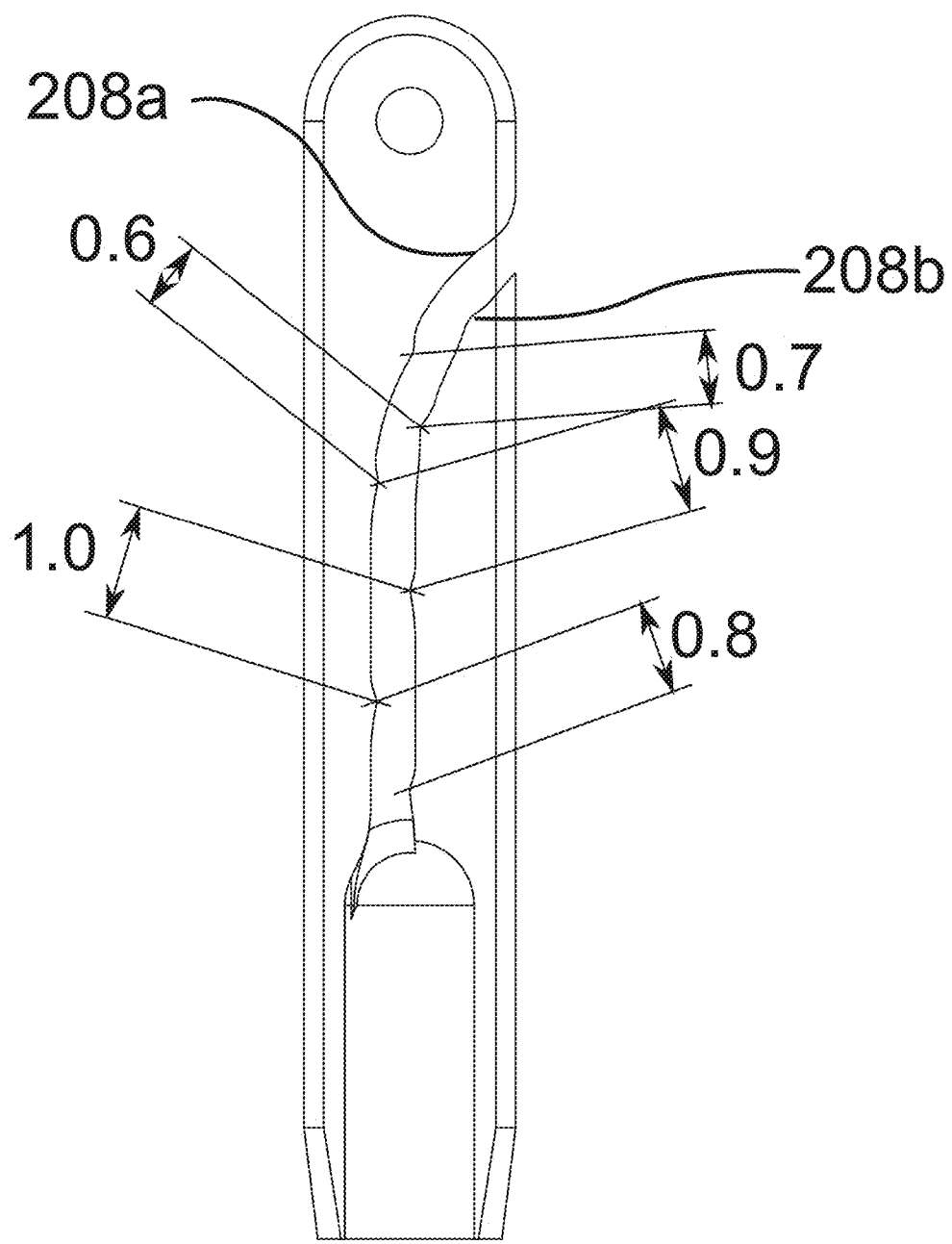

In an exemplary embodiment of the invention, the protrusions may be spaced at non-constant distances from one another, for example, as shown in FIG. 9K, at spacings of about 1, 1.4, and 1.8 mm (e.g. increasing spacing) along lumenal wall 208b (said spacings being between the same protrusions as labeled in FIG. 9J 203g, 203f, 203e and 203d, in order), or 1.2 and 2.0 mm (between protrusions 203c, 203b, and 203a, in order), along opposite lumenal wall 208a. In an exemplary embodiment of the invention, the protrusions on said opposite walls may be staggered, so that said protrusions have their peaks, insofar as the constraints of relative spacing, relative wall length, and protrusion number permit, about in the middle of the spacing between the peaks of protrusions on the opposite wall, thus producing an alternating arrangement of protrusions. In the example as shown in FIG. 9L, the alternate-wall spacings between closest protruding peaks are about 0.8, 1.0, 0.9, 0.6 and 0.7 mm (said spacings being between protrusions 203d, 203a, 203e, 203b, 203f, 203c and 203g, in order). Other spacing sizes and/or variations, for example, smaller or larger, may be provided. Optionally, the spacings are a function of curvature and distance from a center of bending of the sheath.

In some embodiments of the invention, distances between said protrusions are selected to not match distances between structures on the needle 100. In some embodiments of the invention, said not-matching of distances reduces occurrences in which multiple portions of said needle come into contact with the lumenal surface at the same time in motion-impeding interactions. In some embodiments of the invention, the provision of said staggered spacing for protrusions on opposite walls helps ameliorate a potential obstructing effect on the motion of said needle 100 that might be obtained by said protrusions interfering with structures of said needle in wall-opposed pairs.

Figure 9M:
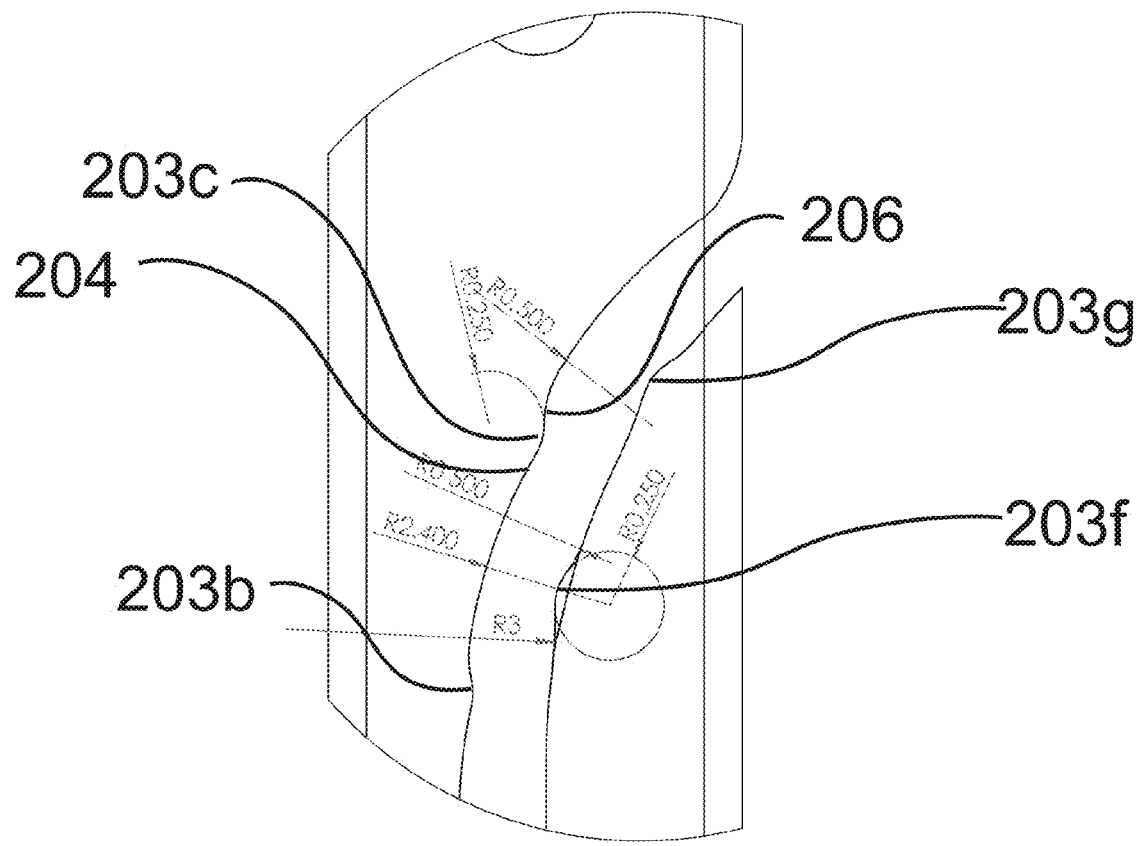
Figure 9N:
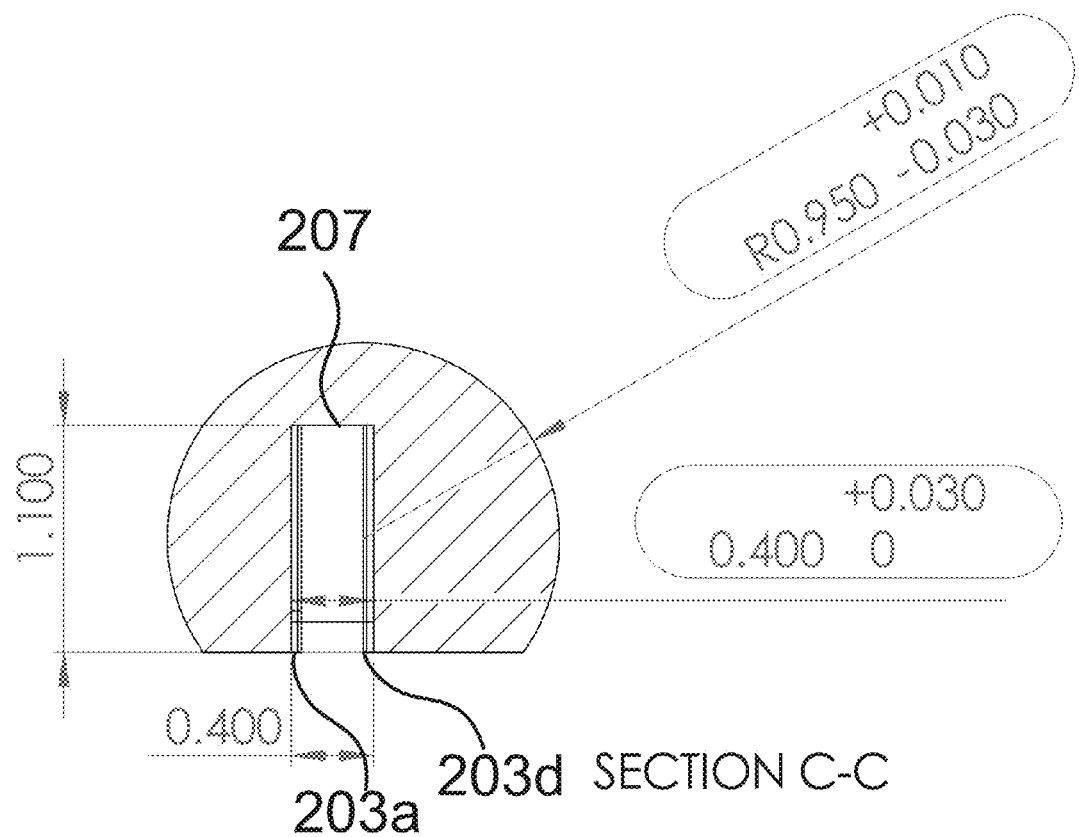

Attention is now drawn to FIG. 9M, which is a magnified version of the circled area of FIG. 9J, according to some exemplary embodiments of the invention. This shows more clearly features of an exemplary embodiment of the invention in which the form of the lumenal surface is undulated, the undulations forming low protrusions. In some embodiments of the invention, protrusions are formed with a shallower grade 204 on the side approached by the needle tip during extension, compared to the opposite side, 206. For example, the initial rise from said floor along said shallower grade may have a curvature with a constant or varying radius between 2.5 mm and 3 mm, while the initial rise from said floor travelling retrograde along the less shallow grade may have a curvature with a constant or varying radius between 0.25 and 0.5 mm.

In some embodiments of the invention, said protrusions 203a-203g from the lumenal surface provide a potential advantage by reducing interactions between the needle and the lumenal surface that may constitute impediments to their relative motion. In some embodiments of the invention, a shallower grade 204 on the side approached by the needle tip during extension provides a potential advantage by ameliorating the condition in which a portion of the needle might catch on the rising curve of the lumenal surface during extension. The steeper grade 206 on the opposite side potentially increases the separation between needle and lumenal surface. In some exemplary embodiments of the invention, the surface is flat with protrusions, rather than being a continuous undulating curve. Optionally, the peaks of the protrusions (e.g., designed to be in contact with the needle) cover less than for example, 30%, 20%, 10%, 5%, 2.5%, or intermediate percentages of the lumen wall surface.

Attention is now drawn to FIG. 9M, which shows a cross section through the cutaway drawing of FIG. 9J, cut through a plane along the dotted line near the middle of the straight section of the sheath head, according to some exemplary embodiments of the invention. In some embodiments of the invention, a flat needle passing through the channel may interact with the lateral walls 207 (the second wall has been cut away in the drawing) to hold it in its closed configuration. Protrusions 203a and 203d are now shown in a profile orthogonal to that of FIGS. 9J-M. Note that the maximum lumen gap between their walls has been widened to 0.4 mm, as compared to 0.34 mm in a previously described exemplary embodiment, shown in FIG. 9D, for example, so a spacing between facing protrusions matches a width of the needle. In some embodiments of the invention, this widening provides a potential advantage by reducing the need for the needle 100 to assume extra bends in order to pass between protrusions. In an exemplary embodiment of the invention, the height of a protrusion, as a function of sheath lumen width is, for example, between 3% and 40%, or, for example, between 5% and 20%.

Figure 9O:
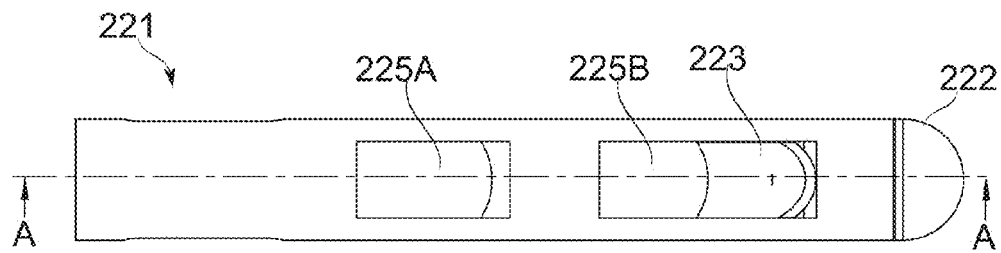
FIGS. 9O-9Q schematically illustrate a lateral-guiding needle sheath head comprising needle guides formed from protrusions bent inward from the sheath head body, according to some exemplary embodiments of the invention.
Figure 9P:
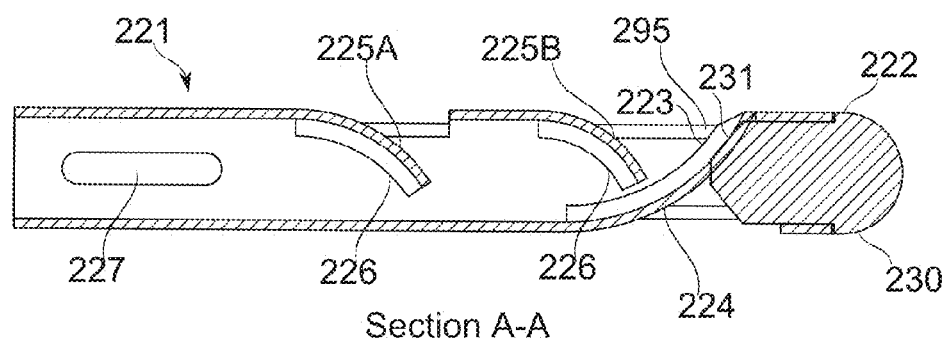
Figure 9Q:
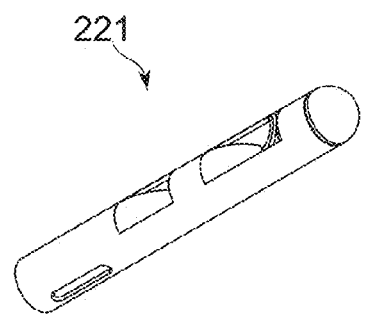

Reference is now made to FIGS. 9O-9Q, which schematically illustrate a lateral-guiding needle sheath head 221 comprising needle guides 225A, 225B, 224 formed from protrusions bent inward from the sheath head body, according to some to exemplary embodiments of the invention. FIG. 9P is a sectional view through line A-A of FIG. 9O; FIG. 9Q is a perspective view.

Figures 9R, 9S:
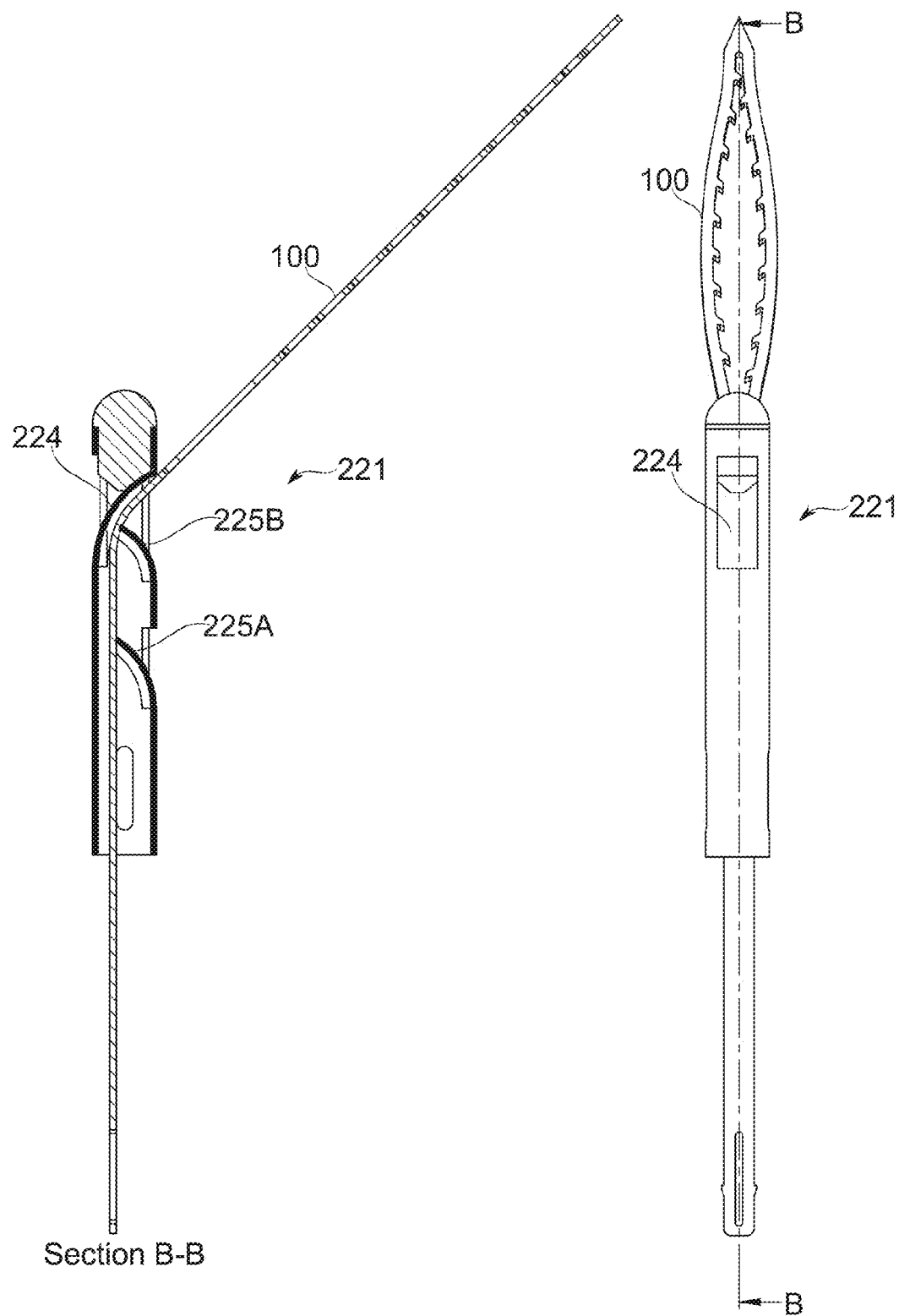
FIGS. 9R-9T schematically illustrate a sheath head in relation to a flexible needle passing therethrough, according to some exemplary embodiments of the invention.
Figure 9T:
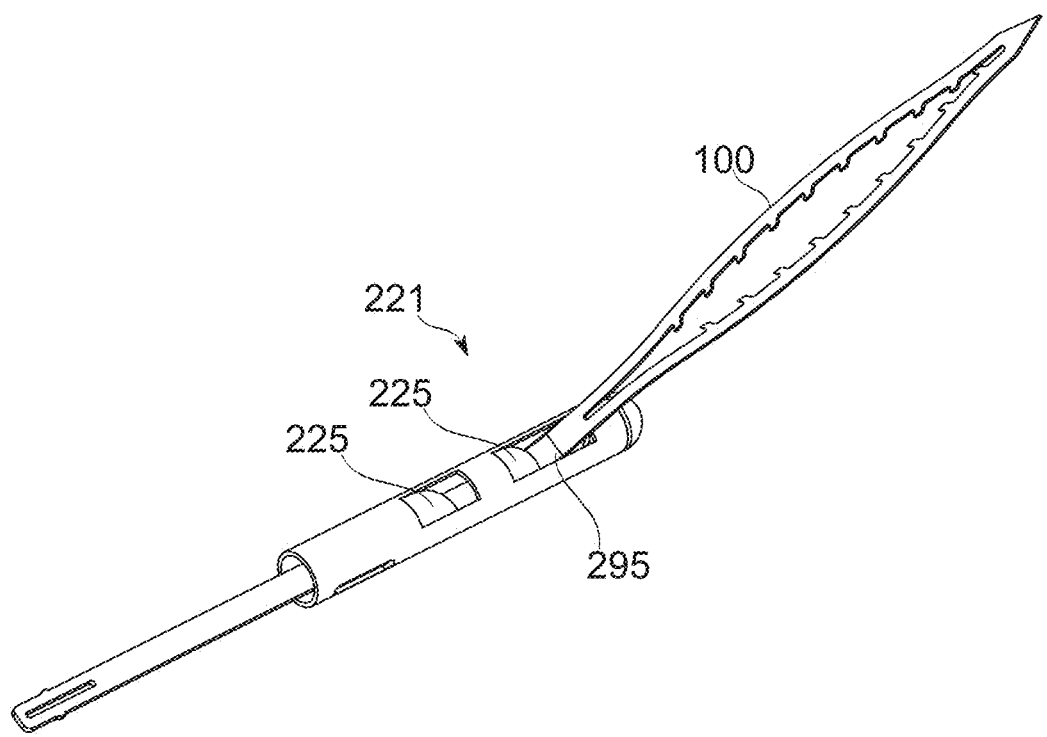

Reference is also made to FIGS. 9R-9T, which schematically illustrate sheath head 221 in relation to a flexible needle 100 passing therethrough, according to some exemplary embodiments of the invention. FIG. 9R is a sectional view through line B-B of FIG. 9S; FIG. 9T is a perspective view.

In some embodiments of the invention, a portion of flat needle 100, 102—or any other flexible needle as described herein—on passing into sheath head 221, is guided by a first needle guide protrusion 225A away from a first side of the lumen of the sheath head 221. In some embodiments of the invention, the first side is also the side of the sheath head comprising a laterally disposed exit port 295 for the needle 100. It is a potential advantage to move the needle away from this side within a more proximal portion of the sheath head 221, such that a given lateral exit angle can be achieved distally by bending the needle 100 through a relatively larger radius of curvature. A larger radius of curvature in turn has the potential advantage of requiring a reduced force to push the needle 100 body through, for example due to reduced deformation resistance by the needle 100 body itself, and/or due to reduced friction against guiding surfaces.

In some embodiments, needle guide 225A is curved on a proximal surface 226 which receives the needle tip, so that distal force for advancing the needle 100 is translated into lateral force tending to move the needle tip to one side of the sheath head 221. In some embodiments, needle guide 225A (and/or other needle guides) comprise flap portions of the wall of the head sheath 221. In some embodiments, the flaps are cut, for example, by laser cutting, and pressed into the lumen, forming guides. Optionally, the cut region appears to be approximately rectangular from the perspective, for example, of FIG. 9O. It is to be understood that trapezoidal, triangular, rounded, and/or other flap shapes are also comprised in some embodiments of the invention.

In some embodiments, the needle 100 is pushed to one side by 50% of a radius of the lumen of the sheath head 221. In some embodiments, the fractional radial displacement is, for example, 10-25%, 20-40%, 30-60%, or another range of displacements having the same, lower, higher, and/or intermediate bounds. In some embodiments, the needle 100 is displaced all the way to the wall of the sheath head opposite the first side of the lumen. It is a potential advantage for the cutaway flap to be long enough to form a graded guide (rather than, for example, a blunt wall), while at the same time remaining short enough so that it retains enough stiffness to force the needle into the desired position. In some embodiments of the invention, the flap length of the needle guide is, for example, 1.2-1.4× the length needed to reach the target displacement distance, 1.3-1.6×, 1.4-2.0×, or another range having bounds equal, larger, smaller, and/or intermediate. Stiffness can also be determined by the width of the flap (along the radial cross-section of the sheath head). Stiffness may be provided, for example, by the material width itself, and/or by the stiffening effects of the flap curvature. It is a potential advantage for the flap width to be wide enough to confer stiffness that displaces the needle to the target position, while being narrow enough that the sheath head is not weakened by the cutout so that it is bent or distorted, for example by passage of the needle therethrough.

In some embodiments, one or more guide surfaces 226, positioned to be encountered by the needle 100 upon insertion, are coated with a friction-lowering layer, for example a polymer resin such as Teflon® (Teflon® is a registered trademark of E. I. du Pont de Nemours and Company). A potential advantage of such a surface treatment is to reduce the resistance of the guides in their capacity as bearings for the passage of a needle. In some embodiments, the outer walls of the guide sheath 221 are comprised of a biocompatible material such as stainless steel, titanium, and/or nitinol.

In some embodiments of the invention, a second and/or subsequent needle guide protrusion 225B also acts to support the needle 100 in its displaced position. Another role of second protrusion 225B is to provide a pivot point nearer to needle angle guide 223, such that the needle 100 is constrained to exit a distal port 295 of the sheath head at a more oblique (lateral) angle to the sheath head longitudinal axis. Optionally, the exit angle of the needle is determined in part by adjusting a position of the tip of needle guide 225, such that a position closer to the contact surface of angle guide 223 and/or deeper within the body of the sheath head 221 results in a more oblique exit angle.

It should be noted that spring forces of the needle 100, in some embodiments of the invention, act to keep needle 100 pushed against guide surfaces 226, for example because needle 100 is anchored at a proximal end thereof in a mounting means which keeps the proximal end of the needle 100 relatively centered within the lumen it occupies. Thus, interactions of needle 100 with the walls of the sheath head 221 are potentially limited to predetermined portions of guide protrusions 225A, 225B, and/or exit guide 224. This potentially reduces impediments to relative motion of needle 100 through sheath head 221, for example, as related to in the descriptions of lumen protrusions in FIGS. 9J-9N hereinabove.

In some embodiments of the invention, exit guide surface 223 is curved opposite the curves of protrusions 225A, 225B. In some embodiments, exit guide 224 comprises a portion of the lumenal wall of the guide sheath 221. In some embodiments, exit guide 224 crosses entirely across the lumen of the guide sheath 221. Optionally, the flap forming exit guide 224 is constructed according to design considerations for flap sized described in relation to guide protrusions 225A, 225B, hereinabove. Optionally, guide surface 223 comprises a low-friction material such as Teflon®.

In some embodiments of the invention, a guide sheath tip 222 is provided at a distal end of the guide sheath 221. In some embodiments, the sheath tip 222 comprises a rounded distal surface 230, or another surface shaped for reducing the occurrence of traumatic injury to tissue during catheter advancement. In some embodiments of the invention, sheath tip 222 comprises a proximal support surface 231, which is positioned to support needle exit guide 224, potentially preventing deformation under the forces of the needle 100 bending where it exits the sheath at distal port 295.

In some embodiments of the invention, the exit angle formed by the needle 100 where it exits distal port 295 is, for example, about 45° away from the longitudinal axis of the sheath head 221. In some embodiments, the exit angle from the longitudinal axis is about, for example, 20-30°, 25-35°, 30-40°, 40-60°, 60-80°, 85-90°, or another range having bounds which are the same, larger, smaller, and/or intermediate. A more oblique exit angle is potentially an advantage for sampling from a wall of a body lumen, and/or for increasing an accessible volume of tissue sampling around the advancing catheter. Potentially, the lateral wall of the catheter helps brace the distal end of the catheter against the insertion forces required for penetration of the needle when the needle exits laterally. In contrast, the bracing received from along the axial length of the catheter, is potentially more prone to buckling under force.

In some embodiments of the invention, sheath head 221 comprises an assembly window 227. Optionally, assembly window 227 is used to verify proper insertion of a sheath 200 into a sheath head 221 (for example, orientation during insertion, and depth during and/or after). In some embodiments, attachment means—for example, adhesive or a fixation member—are passed through window 227 to secure sheath head 221 in position relative to sheath 200.

Flat needles 100 or 102 such as those shown in FIGS. 1, 2, 3, 5, 7, 8, and 9A-9C may optionally be made to be bendable and/or to have at least a bendable distal portion. Such bendable embodiments may be passed through a sheath head 201 or similar structure and thereby be directed in a direction which is lateral with respect to the direction of insertion and/or advance of a sheath 200 which contains them, according to methods taught in PCT '080. Needles 100 may also be constructed with a pre-bent construction (optionally using the nitinol shape memory function), and be formed so as to bend when advanced beyond a distal end of sheath 200.

Attention is now drawn to FIGS. 9E-9I, which provide dimensional information, according to some exemplary embodiments of the present invention. On some of these figures an optional range of sizes is presented, currently considered appropriate for some exemplary embodiments. In other words, the numbers given in the figures describe exemplary ranges of sizes for some exemplary embodiments, but are not to be considered limiting.

For example, in an exemplary embodiment shown in FIG. 9I, the laterally expandable portion of needle 100 may be between 3 and 80 mm long, 20.649 mm being the size of a particular embodiment whose description was the source of this figure. Spine width (back to front) may be between 0.05 mm and 3 mm, teeth height between 0.05 and 5 mm. The closed-configuration side-to-side width of the expandable portion of these embodiments (which is may be similar or equal to the width of non-expandable portions of the needle) is between 0.05 mm and 3 mm.

Note also that in some embodiments, the expandability of the expandable portion is between 2% and 25%. In some embodiments it is between 5% and 20%.

In some embodiments using nitinol, metal thickness of between 0.08 mm and 2 mm is used.

Attention is now drawn to FIGS. 10A-10F, which are figures adapted from photographs of prototypes of embodiments of a needle 102 contained in a sheath 200, having control means 280, 282, and using a sheath head similar to that shown in FIGS. 9D, 9K and/or 9T, according to some exemplary embodiments of the present invention.

Figure 10A:
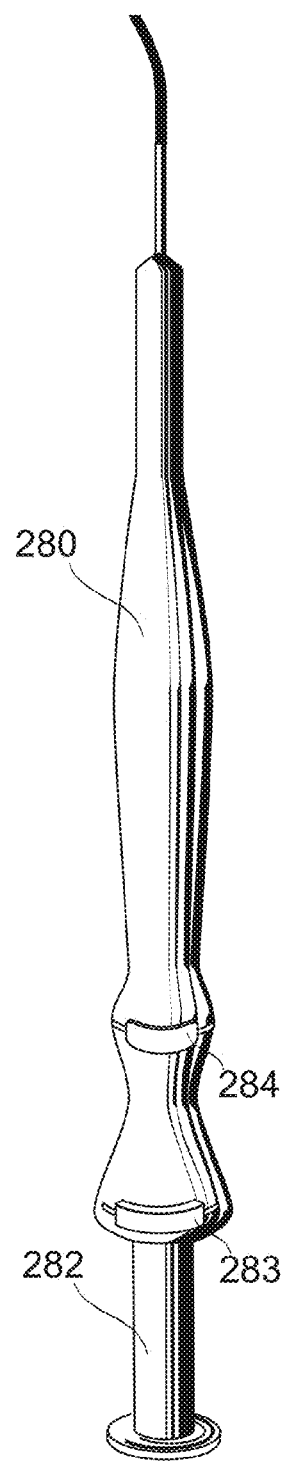
FIG. 10A is a view adapted from a photograph of an embodiment of the present invention showing a proximal handle for a sheath, according to some exemplary embodiments of the present invention.
Figure 10B:
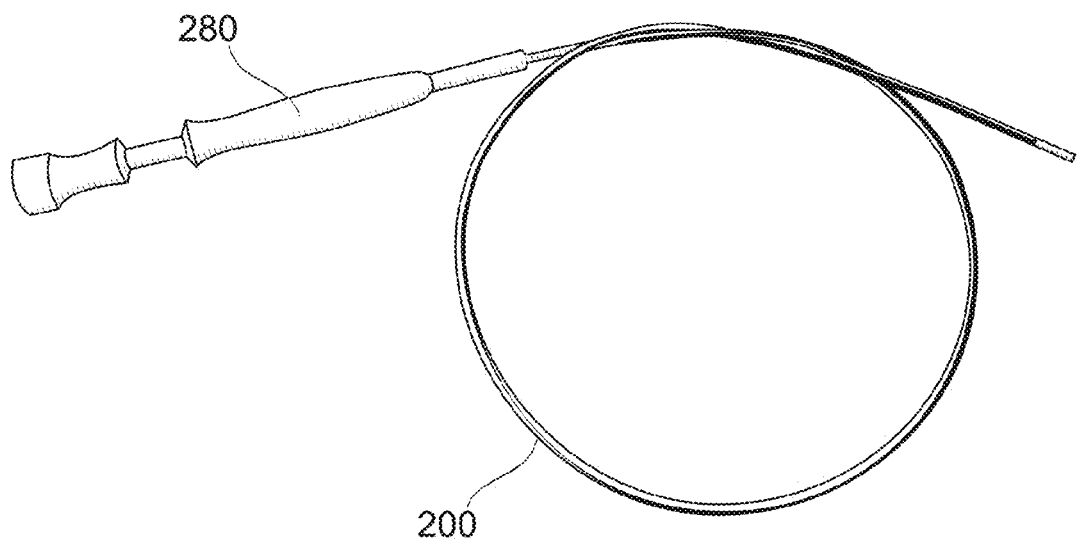
FIG. 10B is a view adapted from a photograph of an embodiment of the present invention showing the handle of FIG. 10A connected to a sheath, according to some exemplary embodiments of the present invention.
Figure 10C:
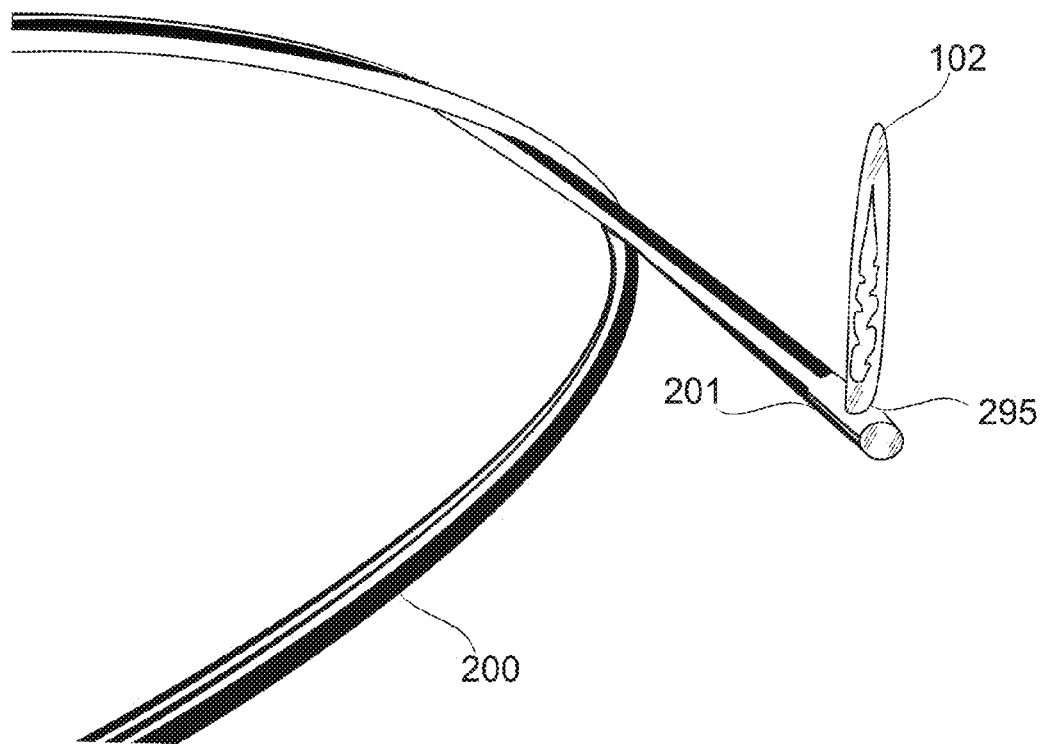
FIG. 10C is a photograph of an embodiment of the present invention showing a flat biopsy needle in open configuration extending from a distal portion of the sheath of the embodiment shown in FIG. 10B, according to some exemplary embodiments of the present invention.
Figure 10D:
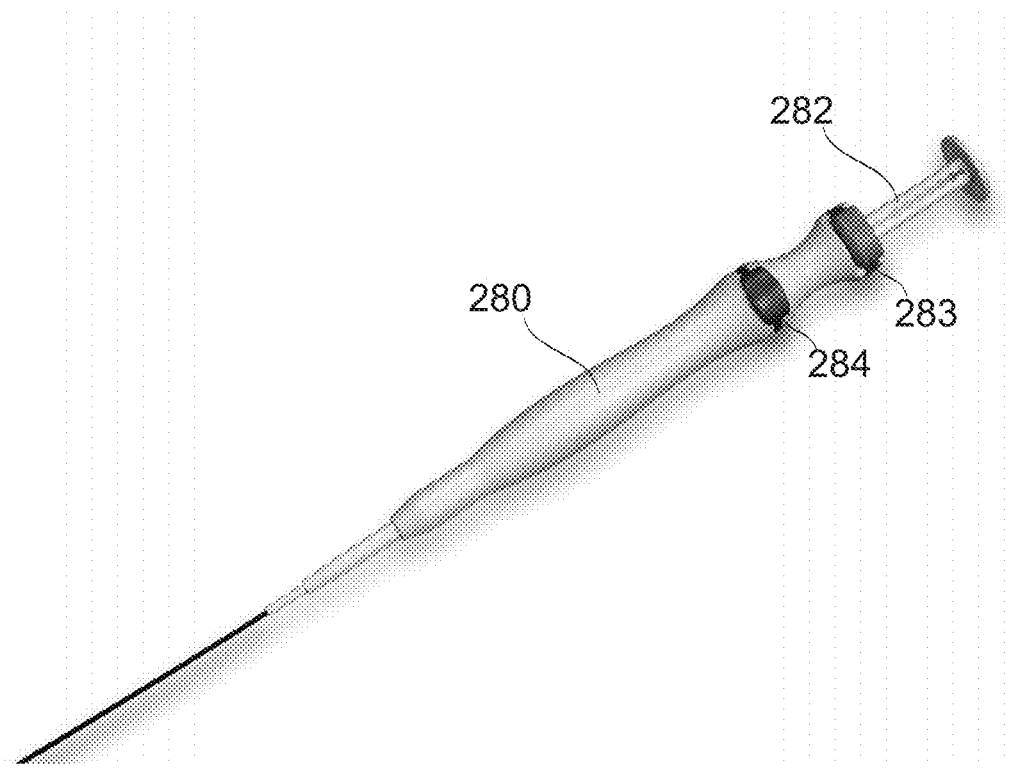
FIG. 10D is a photograph of an embodiment of the present invention showing a proximal handle for a sheath, according to some exemplary embodiments of the present invention.

FIGS. 10A and 10D show a handle 280 comprising a plunger 282 and adapted for advancing a sheath within a body conduit, and subsequently causing a flat needle 102 to extend therefrom. Control buttons 283, 284 are optionally usable to impart, direct, and/or limit needle movement.

Figure 10E:
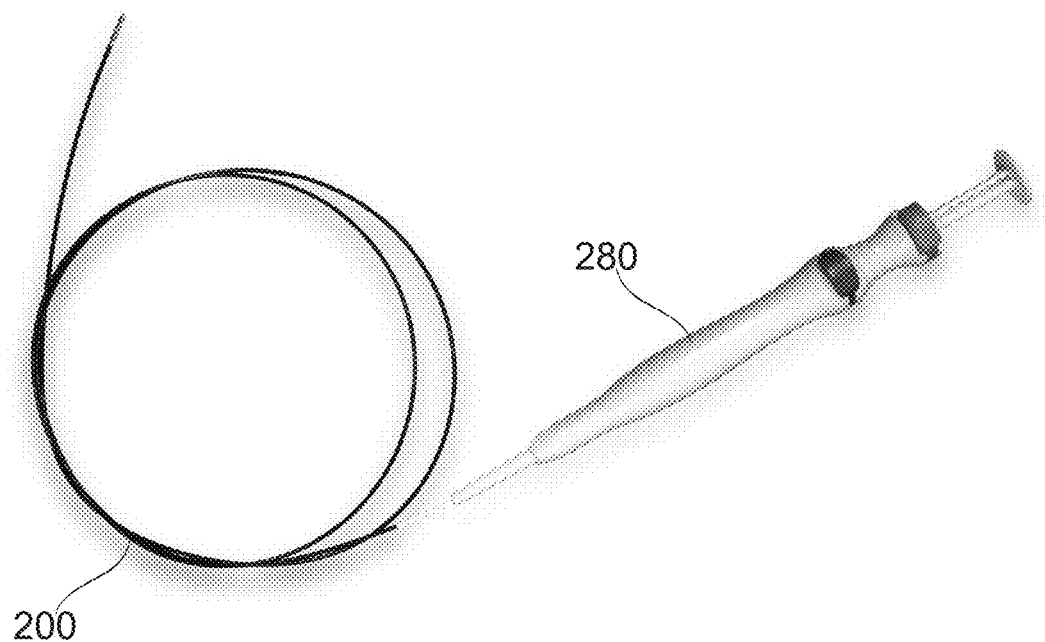
FIG. 10E is a photograph of an embodiment of the present invention showing the handle of FIG. 10D connected to a sheath, according to some exemplary embodiments of the present invention.
Figure 10F:
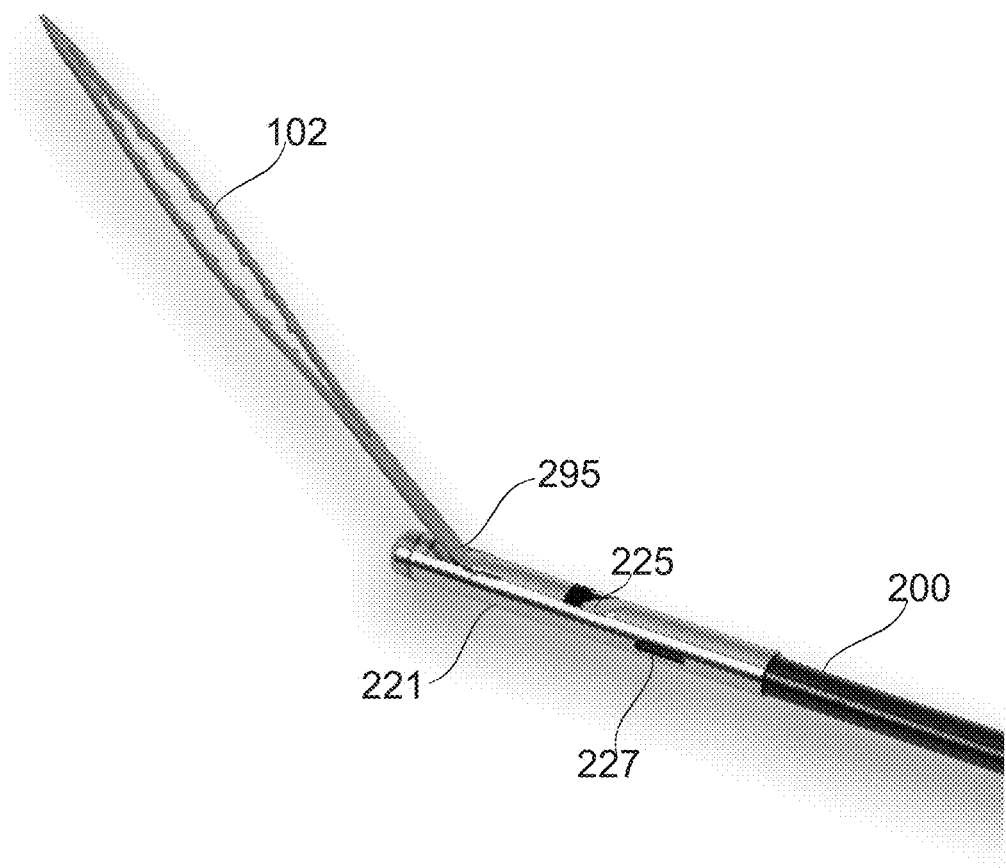
FIG. 10F is a view adapted from a photograph of an embodiment of the present invention showing a flat biopsy needle in open configuration extending from a distal portion of the sheath of the embodiment shown in FIG. 10E, according to some exemplary embodiments of the present invention.

FIGS. 10B and 10E show handle 280 attached to a sheath 200, ready for use. FIGS. 10C and 10F show a needle 102, in open configuration, extending laterally from a distal port 295 of a sheath head 201, 221 connected at a distal portion of a sheath 200. FIG. 10F shows the relationship of sheath head slot 227 to the distal end of inserted sheath 200, and also shows guide protrusion 225.

Figure 11:
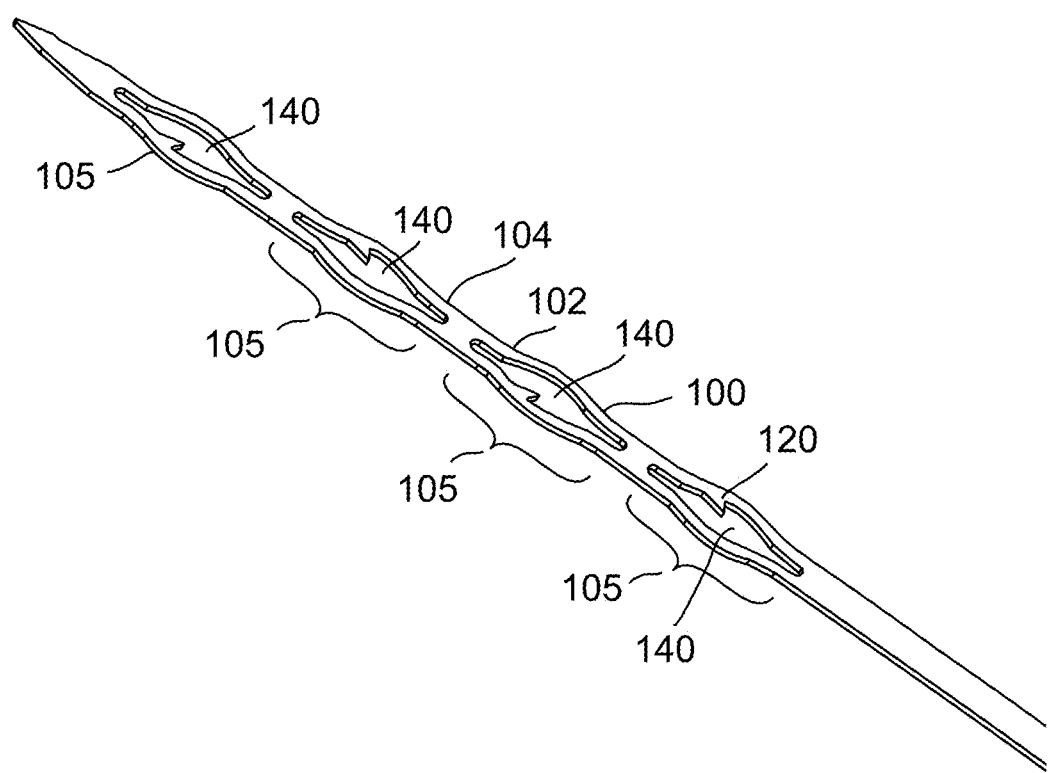
FIG. 11 is a simplified schematic of a multi-aperture flat biopsy needle, according to some exemplary embodiments of the present invention.

Attention is now drawn to FIG. 11, which is a simplified view of a multi-aperture 'flat' (optionally, bendable) biopsy needle, according to some exemplary embodiments of the present invention. Needle 100 in FIG. 11 is also labeled 102 to designate its 'flat' configuration, and also labeled 104 to designate its multi-aperture configuration. As seen in the figure, needle 104 comprises multiple expandable portions 105 optionally arranged serially along a length of needle 104, each providing an inner space 140 when in an opened configuration, as shown in FIG. 11.

Figure 12:
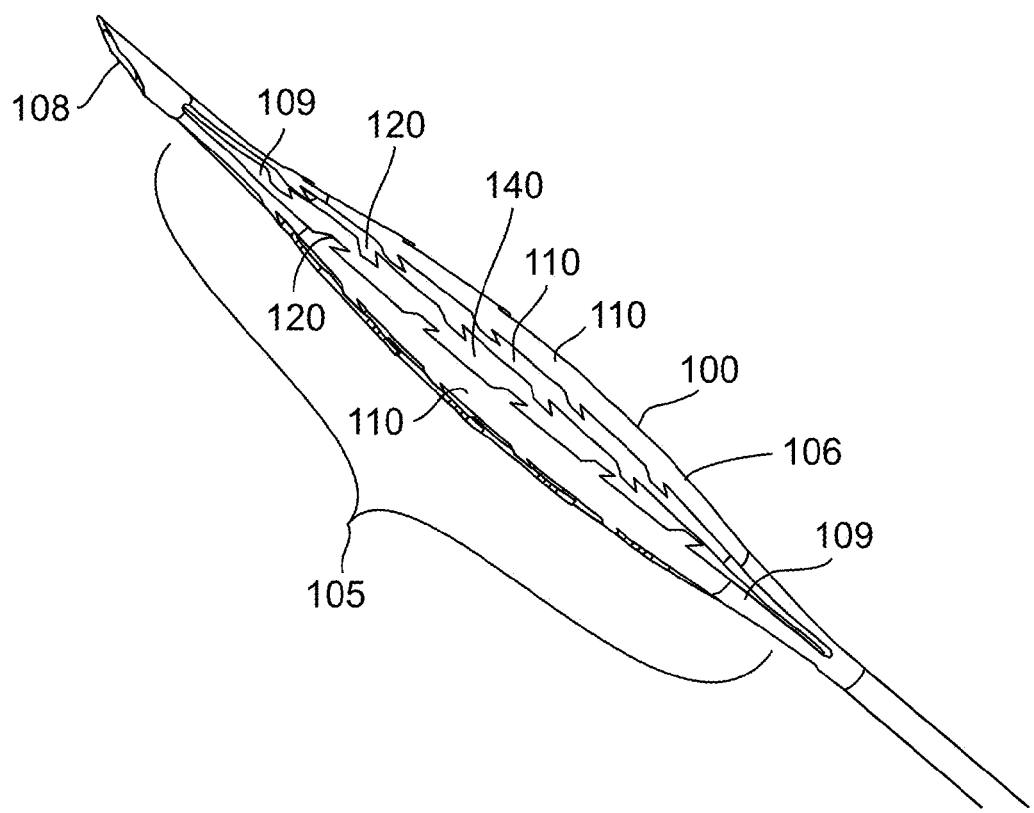
FIGS. 12, 13 and 14 are views of multi-spined biopsy needles in open configurations, according to some exemplary embodiments of the present invention.
Figure 13:
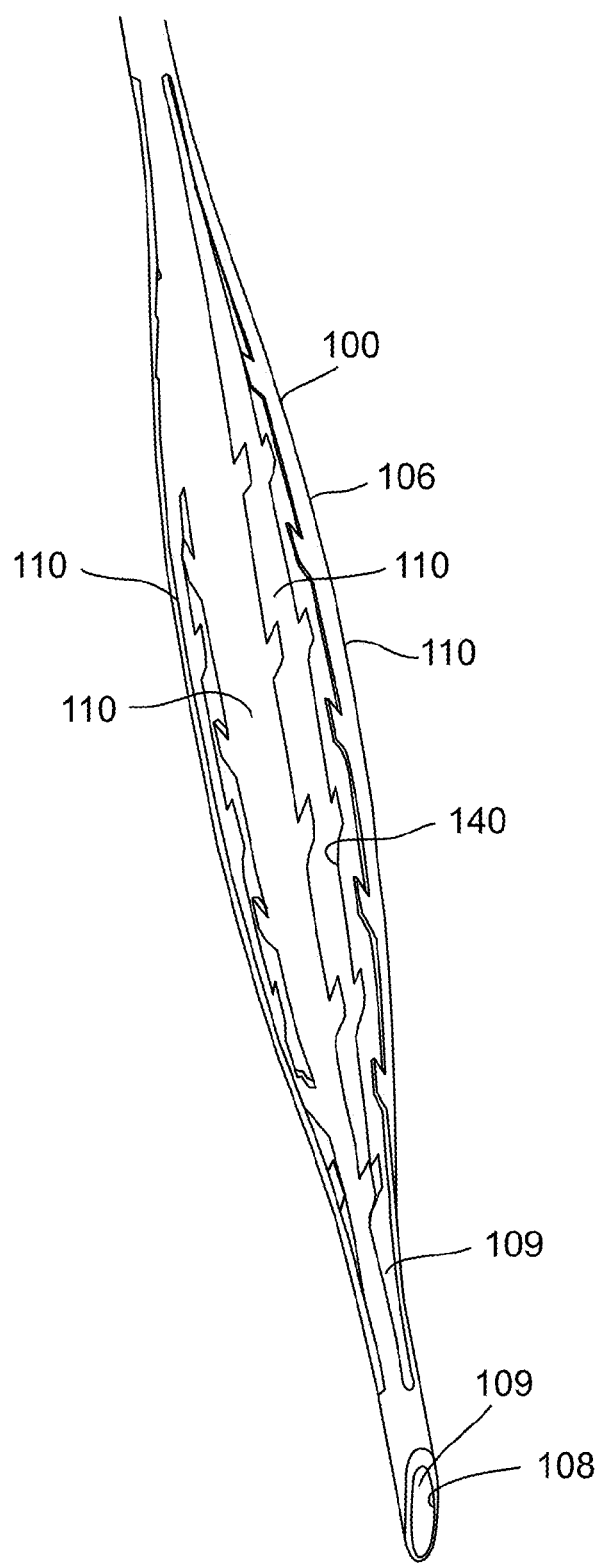
Figure 14:
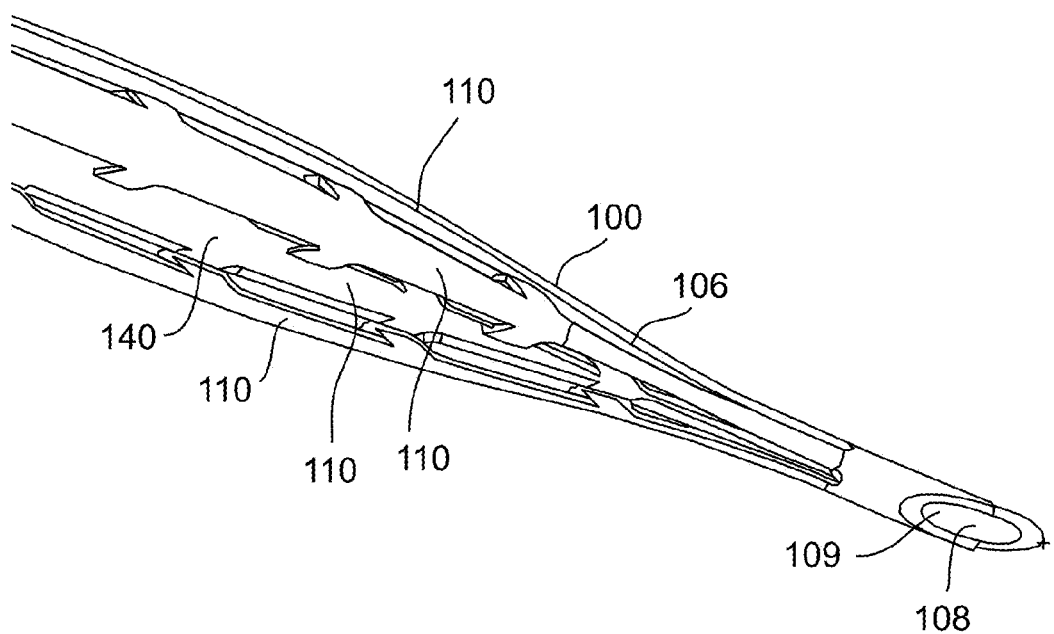
Figure 15:
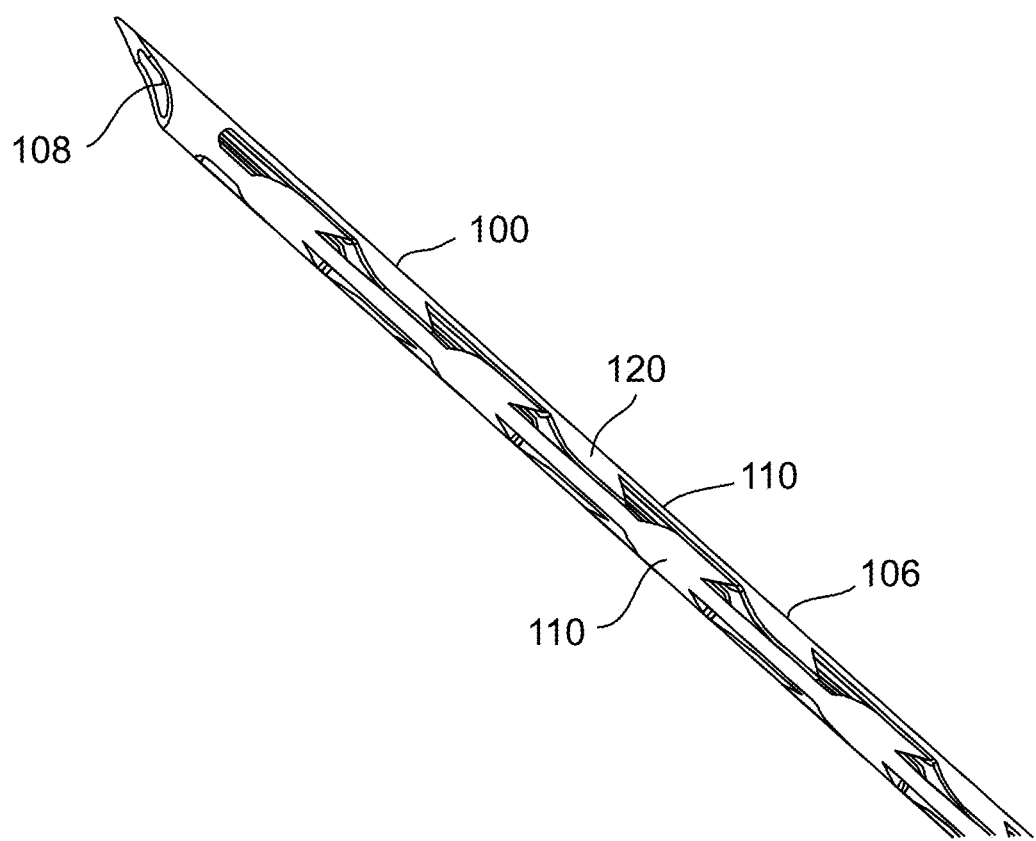
FIG. 15 is a view of the needle of FIG. 12 in closed configuration, according to some exemplary embodiments of the present invention.

Attention is now drawn to FIGS. 12, 13, and 14 which show views of multi-spined needles 100, labeled 106 to designate the multi-spined feature, according to embodiments of the present invention. Attention is also drawn to FIG. 15, which presents the needle 106 of FIG. 12 in closed configuration.

Herein, the term "multi-spined" is used to designate three or more spines, and therefore distinguishes multi-spined needles 106 from flat (and therefore optionally easily bendable) needles 102 described hereinabove.

As shown in FIGS. 12-15, multi-spined needles 106 comprise more than two spines 110. Embodiments with 4 spines each are shown in these figures, but that number of spines is exemplary only, and needles having 3 spines (not shown), having 4 spines (as shown in FIGS. 12-15), and having 5 or more spines (not shown) are contemplated. In some embodiments spines 110 of needles 106 expand laterally outward when freed of constraint by a sheath 200, each spine optionally expanding away from a central longitudinal axis of needle 106, thereby creating an inner space 140 as shown. Tissues caught within inner space 140 while needle 106 is in open configuration are trapped within needle 106 when needle 106 is squeezed back to its closed configuration by centripetal lateral pressure from sheath 200

(i.e. when a previously extended distal portion of needle 106 is retracted into sheath 200 or when sheath 200 is advanced to cover a previously extended distal portion of needle 106, as discussed above).

Since multi-spined needles 106 tend to be less bendable than flat needles 102, multi-spined needles are typically extended straight from a containing sheath 200 (as shown in FIGS. 3 and 5), rather than in a lateral direction as is optionally possible with flat needles 102, as shown in FIG. 10C.

In some embodiments of needles 106, space is provided for an internal passageway 109 optionally ending in a distal orifice 108 of needle 106. Internal passageway 109 may optionally be sized to provide passageway for a tool and/or a fiber optic element and/or a conduit for a fluid such as an irrigation fluid or a medication or an ink. Alternatively, passageway 109 may be used to convey a tool or a material to or from a biopsy site. If passageway 109 is present, teeth 120 and spines 110 are sized and positioned so as to provide space for passageway 109.

Biopsy Needle and Catheter Attachment

Figure 16A:
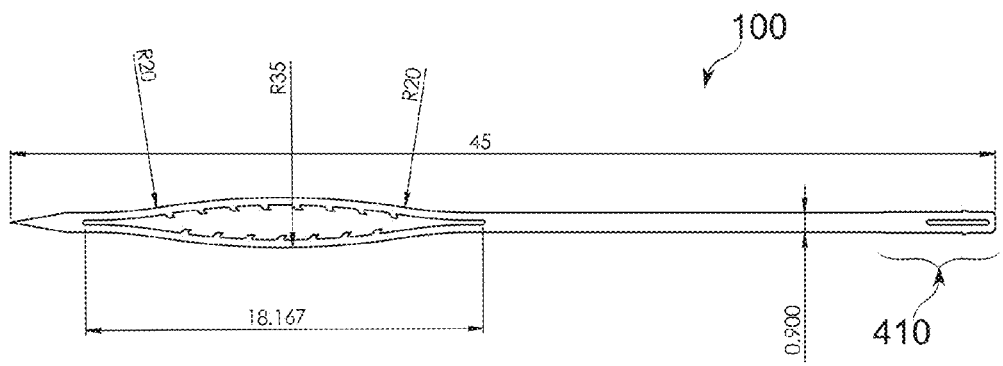
FIGS. 16A-16B schematically illustrate an exemplary biopsy needle including details of a base end attachable to a catheter shaft, according to some exemplary embodiments of the present invention.
Figure 16B:
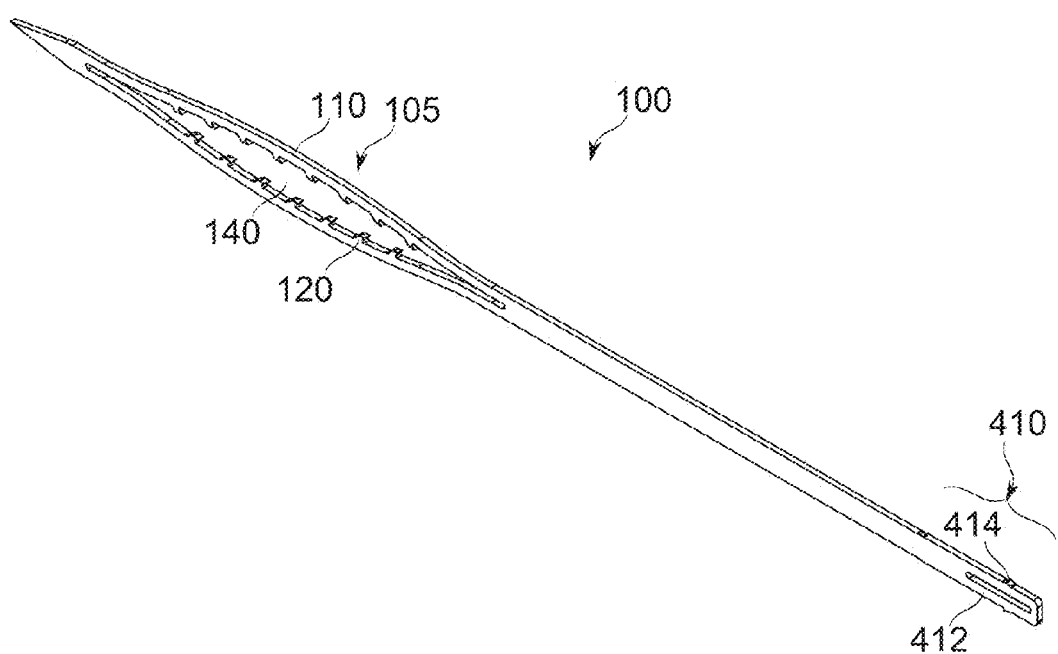

Reference is now made to FIGS. 16A-16B, which schematically illustrate an exemplary biopsy needle 100, including details of a base end 410 attachable to a catheter lead, according to some exemplary embodiments of the invention.

In some embodiments of the invention, base end 410 is separated from expandable area 105 by a relatively short tang, for example, 20-40 mm in length. In some applications of some embodiments, this length is long enough for a needle to be directly held at the base end reach a target location, for example, for biopsy. In some embodiments, the tang extending toward the base end 410 from expandable region 105 is longer, for example, 50-100 mm, 80-160 mm, 150-300 mm, or another longer or shorter distance. In some embodiments, length is added by another portion attached to the base end 410 of the needle 100. Potentially, using a two-piece design provides an advantage by allowing the pushing portion of the needle assembly to have mechanical properties independent of those of the needle. The mechanical properties may be chosen, for example, for flexibility, pushability, and or/steerability. Optionally, a two-piece design allows a needle to be replaceable on a pusher lead. Optionally, a two-piece design increases the versatility of a shorter needle by allowing it to be used for sampling at a greater distance from a point of manipulation and control.

In some embodiments of the invention, the proximal or base end 410 of needle 100 is configured to attach to a receiving portion of a catheter lead for attachment thereto, for example by insertion. Spring member 412 is sufficiently elastic to bend under lateral pressure during assembly to the catheter lead, and then to spring back, pushing catch 414 into a receiving area. In some embodiments of the invention, spring member 412 is sufficiently flexible that needle 100 can be inserted to a receiving portion 592 of a catheter lead without a requirement for force that buckles the catheter lead. In some embodiments, the force of insertion is about, for example, 1-3 N, 2-5 N, 4-8 N, 5-10 N, 8-16 N, or another range of forces having the same, greater, lesser, and/or intermediate bounds. In some embodiments—due, for example, to the catch shape—the force required to directly pull the needle from its insertion point is a multiple of the force required for insertion greater than one. In some embodiments, the multiple is, for example, about 3-5×, about 4-8×, about 6-10×, or another range of multiples having the same, greater, lesser, and/or intermediate bounds.

In some embodiments, the catch-secured attachment of the needle to the catheter lead prevents the needle from accidentally dislodging during a biopsy procedure. This is detailed in relation, for example, to FIGS. 20A-20E. In some embodiments, the needle is releasable intact from the catheter lead after sampling. This provides a potential advantage so that the sample carrying portion of the needle can be readily detached for placement in preservation storage without a requirement for an additional tool and/or cutting operation. In some embodiments of the invention, a needle is rapidly replaceable to a catheter lead. This is a potential advantage, for example during procedures in which more than one biopsy sample is to be taken.

Exemplary measurements associated with dimensional indications here and in the other figures herein are in millimeters. The exemplary needle of FIGS. 16A-16B, for example, is 45 mm long, with the inner lumen 140 of expandable area 105 being 18.167 mm long. The outer edges of spines 110 in the open position follow merged curves of radius 20 mm, 35 mm, and 20 mm working toward the tip. The center of curvature alternates sides of spine 110 in passing along the three curvatures listed. These dimensions are exemplary, and are the same, larger or smaller, according to the particular embodiment and/or the conformational state of the needle (for example, 10% larger or smaller, 20%, 50% or another relative size). Exemplary ranges for needle dimensions are given, for example, in relation to _FIG. 9I_.

Figure 17A:
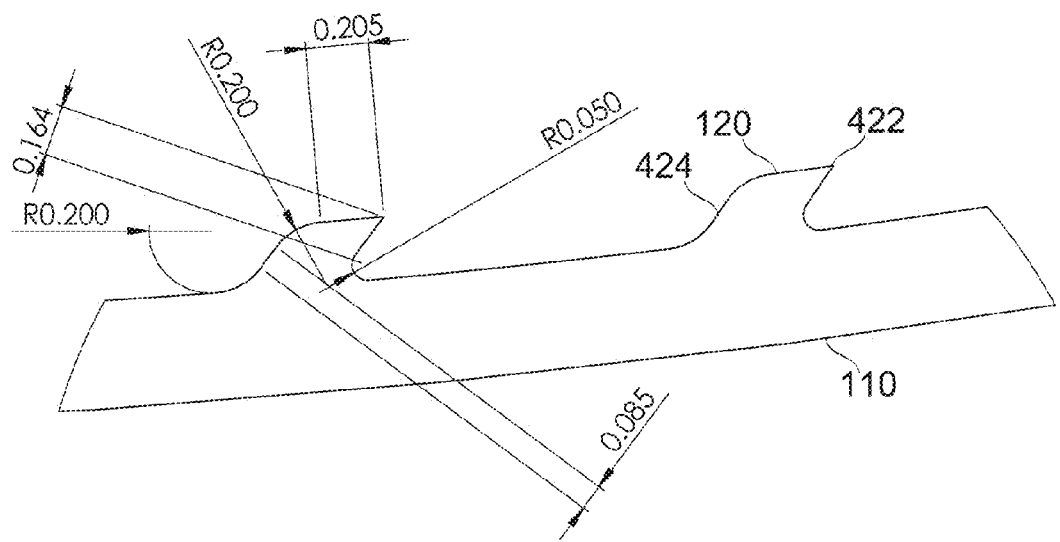
FIGS. 17A-17C schematically illustrate details of the construction of an exemplary biopsy needle, according to some exemplary embodiments of the present invention.
Figure 17B:
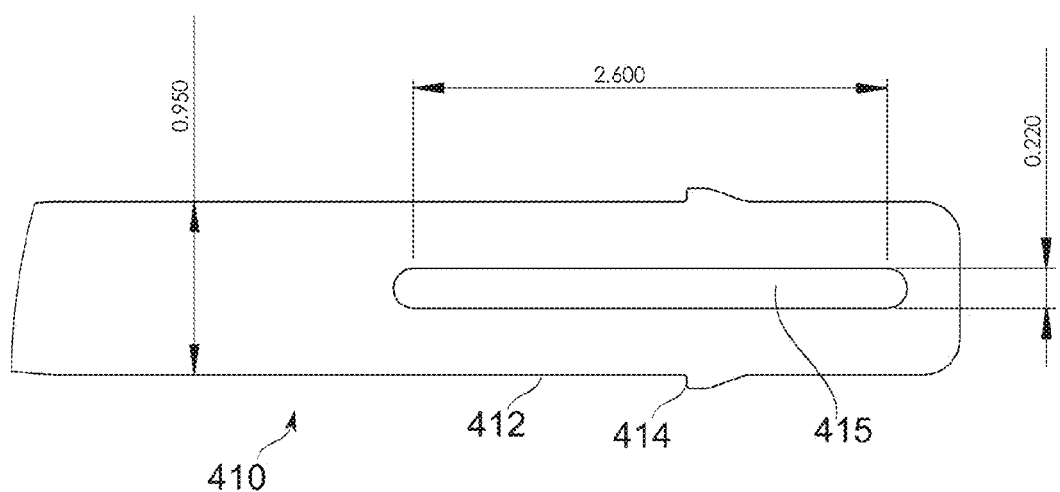
Figure 17C:
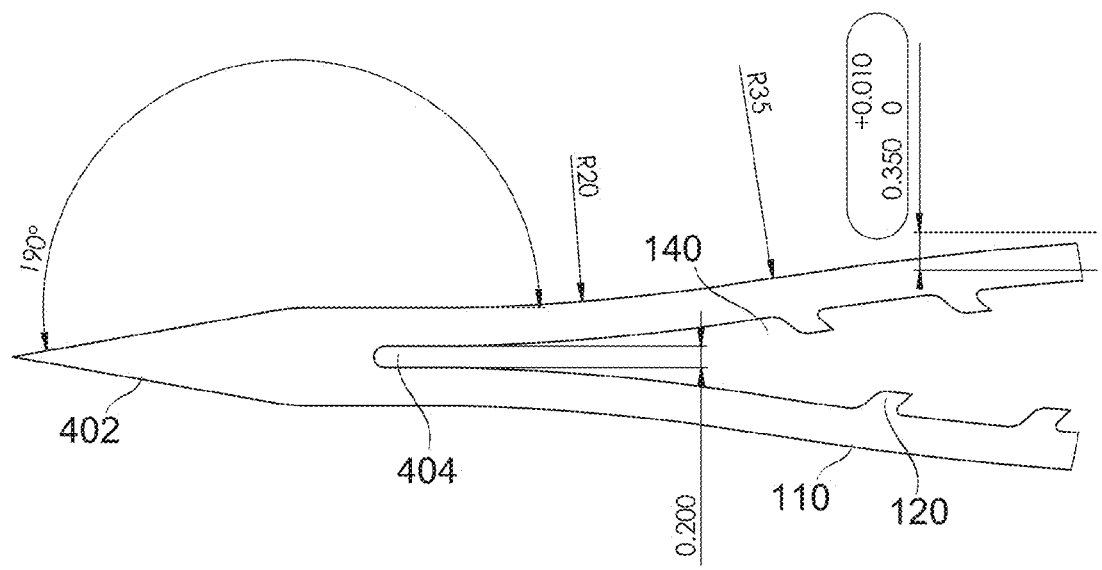

Reference is now made to FIGS. 17A-17C, which schematically illustrate details of the construction of an exemplary biopsy needle 100, according to some exemplary embodiments of the invention. In FIG. 17A, a tooth 120 is shown in expanded detail, attached to spine 110, in accordance with some exemplary embodiments of the invention. In this example of a tooth, a cutting edge 422 is to distinguished with a sharpened point for snagging and/or cutting tissue. The distal tooth edge 424 is rounded. Potentially, a smoother distal profile assists entry with lowered force during tissue penetration.

In FIG. 17C, details of the distal tip of needle 100 are shown in expanded detail. In some embodiments of the invention, the extreme distal tip of the needle 100 comes to an acute point 402. The acute point 402 is leading during penetration of tissue. In some embodiments, a slit region 404 is cut near the tip region, extending distal from inner space 140. Optionally, the extension slit 404 allows the spines 110 to flex inward, for example during insertion, to enter the penetration hole made by tip 402. Potentially, this reduces the insertion force required for penetration. According to the embodiment, the maximum force needed for insertion is, for example, 5%, 10%, 20%, or 40% of the force required to dislodge needle 100 from its attachment. This maximum force may also be any value in between, or a larger or smaller force. Optionally—for example, if the needle encounters an impenetrable barrier—the needle and/or another component of the system flexes to absorb force which could potentially dislodge the needle.

In FIG. 17B, the base end 410 of needle 100 is shown in expanded detail, including spring member 412 and catch 414. In some embodiments of the invention, spring member 412 is formed by cutting an aperture 415 from the base end. The removal of material permits spring member 412 to flex toward the interior under pressure.

Reference is now made to FIGS. 18A-18D, which schematically illustrate an assembled biopsy needle catheter lead, according to some exemplary embodiments of the invention.

Figures 18A, 18B, 18C, 18D:
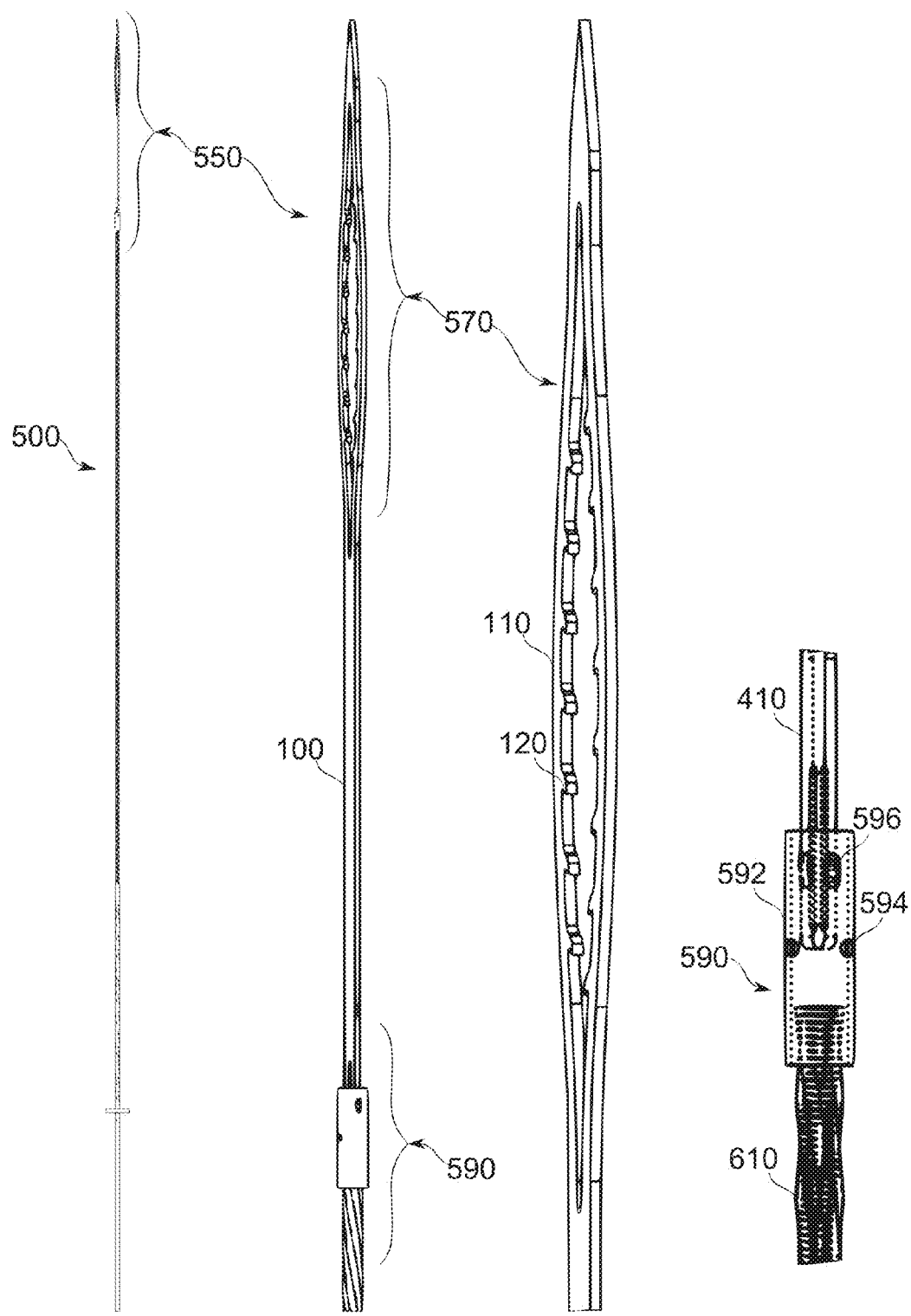
FIGS. 18A-18D schematically illustrate an assembled biopsy needle catheter shaft, according to some exemplary embodiments of the present invention.

FIG. 18A shows an assembled catheter lead 500 in overview. Distal catheter lead region 550 is shown expanded in FIG. 18B, and comprises the needle 100, including needle loop region 570, and needle attachment region 590. Loop region 570 is expanded further in FIG. 18C, where spines 110 and teeth 120 are visible. Needle attachment region 590 is shown expanded in FIG. 18D.

In some embodiments, needle attachment region 590 comprises the base end 410 of the needle 100, needle attachment ferrule 592, and a distal end of push wire 610. Ferrule 592 comprises ferrule ports 594, and ferrule notches 596, as well as receiving apertures for the needle base end 410 and the push wire 610 distal end. In some embodiments, ferrule 592 is made of a biocompatible metal, for example stainless steel or titanium.

Figure 19:
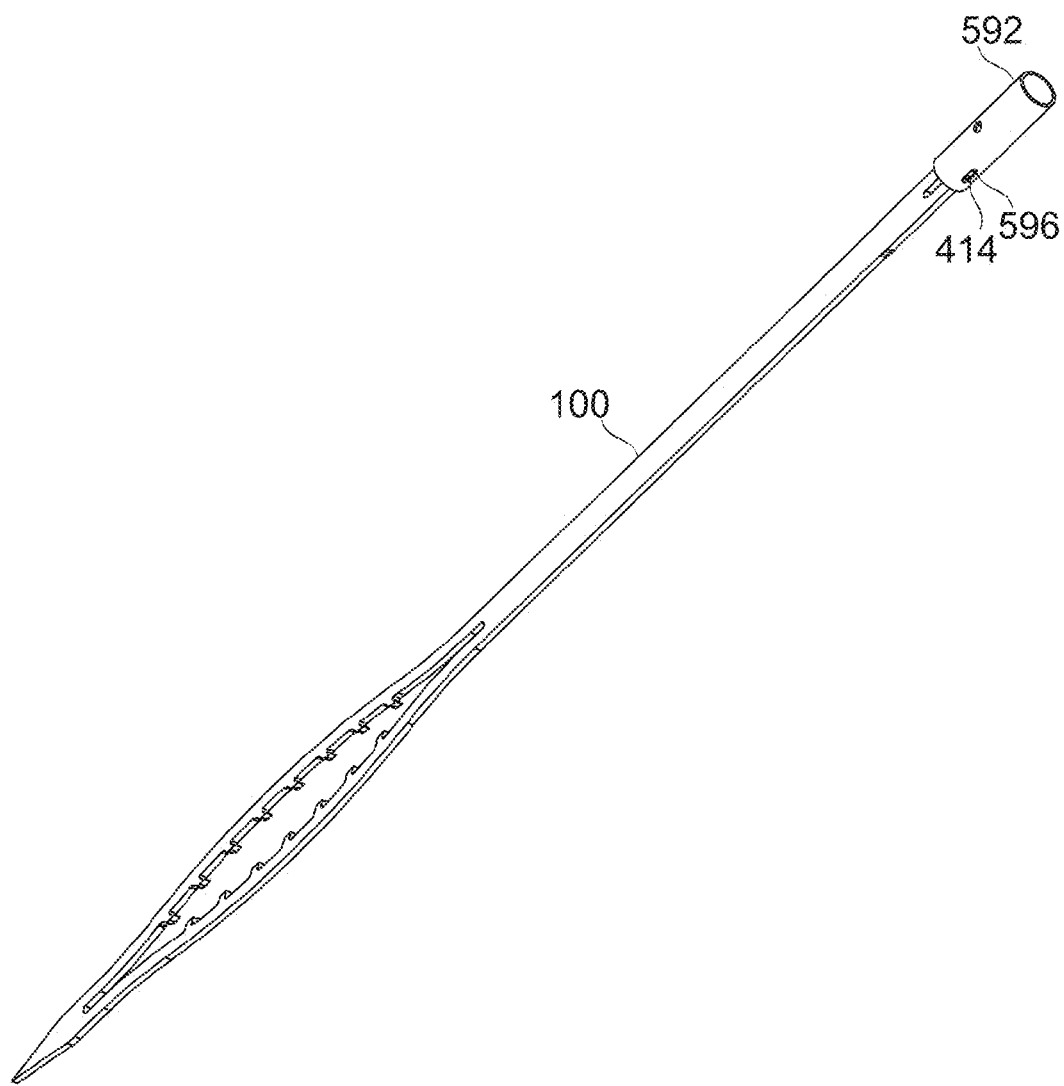
FIG. 19 schematically illustrates a needle assembled to a needle attachment ferrule, according to some exemplary embodiments of the present invention.
Figure 21A:
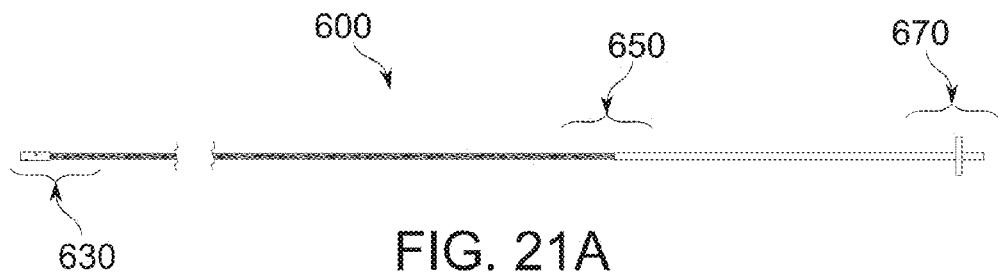
FIGS. 21A-21D schematically illustrate details of exemplary proximal (base) regions of a biopsy needle catheter shaft, according to some exemplary embodiments of the present invention.
Figure 21B:
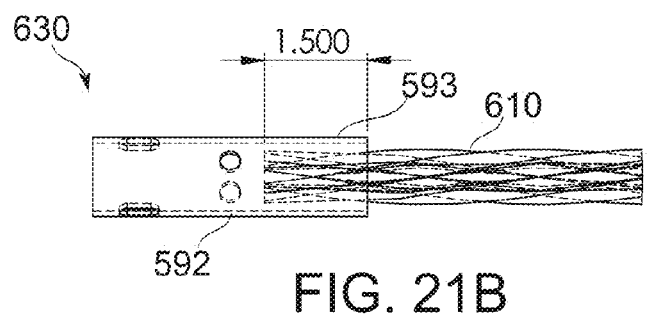
Figure 21C:
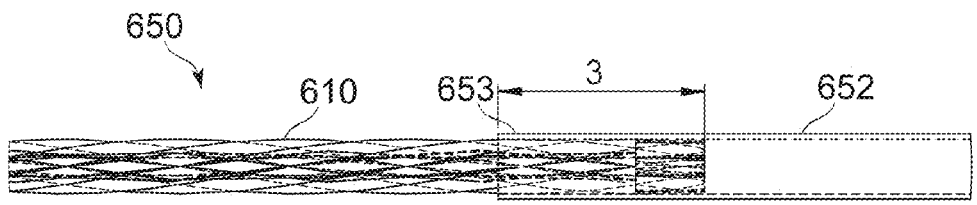
Figure 21D:
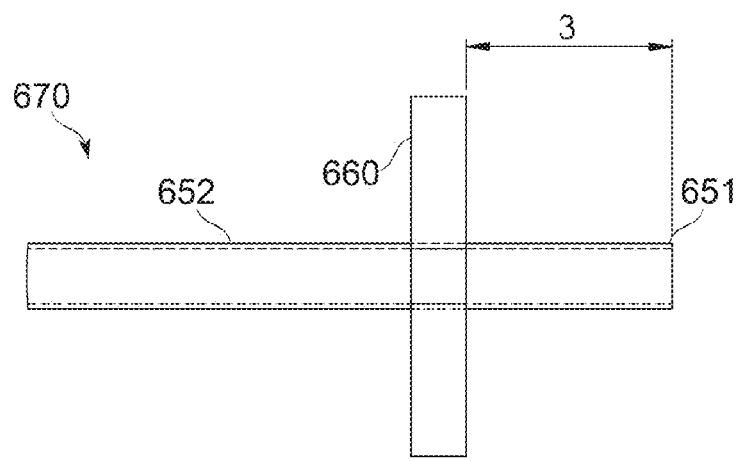

Reference is now made to FIG. 19, which schematically illustrates a needle 100 assembled to a needle attachment ferrule 592, according to some exemplary embodiments of the invention. The exemplary attachment comprises insertion of catch 414 into notch 596. Reference is further made to FIGS. 20A-20E, which are schematic views of attachment structures in detail, according to some exemplary embodiments of the invention.

FIG. 20A shows the wide side of the needle 100, and FIG. 20B illustrates details of attachment region 591 from the same viewing angle for some exemplary embodiments of the invention. FIG. 20D is a view of the narrow edge of the needle, and FIG. 20E shows details from this viewpoint for some exemplary embodiments of the invention. FIG. 20C shows the needle 100 and ferrule 529 assembly looking along the needle 100 from the tip for some exemplary embodiments of the invention.

In some embodiments, needle attachment region 591 comprises features for attaching and maintaining attachment of biopsy needle 100 to a catheter lead base via ferrule 592. Attachment is by the insertion of needle catch 414 into ferrule notch 596. In some embodiments, the needle in the region of catch 414, when unconstrained, is wider than the lumenal wall of ferrule 592. During insertion, spring member 412 flexes inward, providing the clearance necessary for catch 414 to enter the ferrule lumen. Optionally, flexing is urged to the spring by the gradually expanding leading surface of catch 414.

In some embodiments, needle 100 narrows abruptly at the back surface of catch 414. Once this narrowing passes the distal edge of notch 596, the catch 414 springs outward again, inserting catch 414 into notch 596. After insertion, the needle 100 cannot be pulled straight out of its attachment position, due to the shape of catch 414.

In some embodiments of the invention, one or more ports 594 are provided, through which the base edge 411 of the needle can be viewed during assembly. Potentially, this assists assembly by making it possible to verify the depth to which the needle base edge 411 has penetrated the receiving aperture of ferrule 592.

Optionally, the structures described for connecting needle 100 to ferrule 592 are operable to disconnect the needle. Disconnection occurs, for example, to allow putting the needle into preservation storage after a biopsy. Disconnection also makes room for a new needle on the same push wire, if a second sampling is to be made.

In some embodiments, to disconnect the needle from the ferrule, the needle base end 411 is pushed further into the receiving aperture of ferrule 592, for example by gripping the shaft of needle 100 with fingers or a gripping tool and pushing the needle 100 proximally. In some embodiments, spring member 412 flexes inward under stress, allowing catch 414 to exit ferrule notch 596. Once catch 414 is clear of notch 596, a relative rotation applied between needle 100 and ferrule 592 puts notch 596 and catch 414 out of alignment. It is then possible to pull needle 100 straight out of the receiving aperture of the ferrule 592, disconnecting the two components.

Reference is now made to FIGS. 21A-21D, which schematically illustrate details of exemplary proximal (base) regions of a biopsy needle catheter lead, according to some exemplary embodiments of the invention. Proximal catheter lead section 600 comprises the needle attachment ferrule region 630, the region of attachment 650 of catheter lead push wire 610 with main wire 652, and base region 670.

In some embodiments of the invention, push wire 610 comprises a braided metal wire mesh. In some embodiments, braided mesh of push wire 610 comprises, for example, stainless steel, nitinol, and/or titanium. In some embodiments, the braided mesh is sufficiently stiff to communicate insertion force to needle 100. In some embodiments, the braided mesh is sufficiently flexible to be threaded through a contorted passageway, such as a blood vessel or portion of a digestive tract. In some embodiments of the invention, the push wire 610 is sufficiently stiff to overcome resistance from tissue against penetration by the needle tip and/or sampling region. In some embodiments of the invention, the required penetration force is, for example, 2-4 N, 3-6 N, 4-8 N, 5-15 N, or another range of forces having bounds which are the same, smaller, larger, and/or intermediate. In some embodiments of the invention, the catheter is sufficiently flexible overall to assume (without impairment of function) a radius of curvature equal or less to, for example, 10 cm, 5 cm, 2.5 cm, or another larger, smaller, and/or intermediate radius of curvature.

In some embodiments of the invention, push wire 610 inserts into receiving aperture 593 of ferrule 592. In some embodiments, catheter lead push wire 610 inserts into receiving aperture 653 of main wire 652. Insertions are secured, for example, by a friction fit, by welding, by adhesive, and/or by securing hardware such as a pin or shim. Optionally, the insertion is reversed; for example the braid of push wire 610 is separated to fit over ferrule 592. There is a potential advantage, however, to a configuration which shields the ends of the push wire, for example, to prevent snagging or loosening.

In some embodiments, main wire 652 comprises, for example, stainless steel, nitinol, and/or titanium construction. In some embodiments of the invention, a control plate 660 is attached near the proximal terminal 651 of main wire 652. Control plate 660 provides a larger surface for the application of control forces to the catheter lead, for example, pushing, pulling, and torquing forces. Optionally, plate 660 also provides a stop, which limits motion of the catheter lead relative to a handle 280 when it presses against portions thereof.

Figure 22:
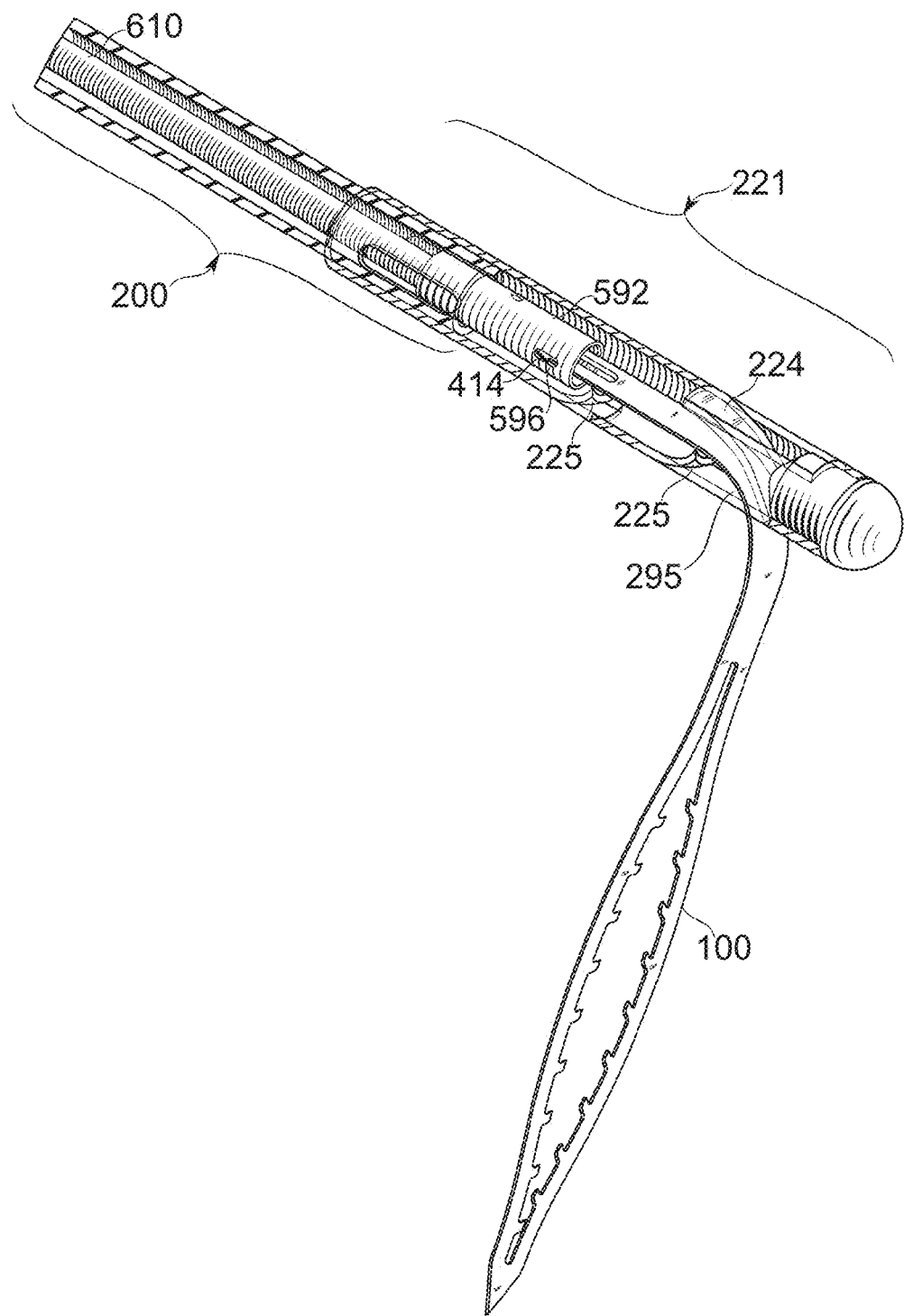
FIG. 22 schematically illustrates an assembly comprising a biopsy needle attached through a ferrule to a push wire near the region where the needle passes out of a sheath head, according to some exemplary embodiments of the present invention.

Reference is now made to FIG. 22, which schematically illustrates an assembly comprising a biopsy needle 100 attached through ferrule 592 to a push wire 610, near the region where the needle passes out of a sheath head 221. FIG. 22 is shown in partial transparency and partial cutaway to illustrate features of some embodiments of the invention as they relate to one another in operation.

In some embodiments of the invention, catheter sheath 200 is inserted into sheath head 221. Ferrule 592 attached at a distal end of push wire 610 is optionally passable distally from sheath 200 to enter sheath head 221. In some embodiments, biopsy needle 100 is attached—for example by means of catch 414 and/or ferrule notch 596—to ferrule 592. Control of the radial position of a portion of needle 100 advancing through sheath head 221 is achieved, for example, by needle guides 225. to Needle guides 225 potentially also act to reduce frictional interactions of needle 100 with the lumen of the sheath head 221. In some embodiments, needle exit guide 224 deflects needle 100 to exit the sheath head 221 via exit port 295. In some embodiments, a portion of the body of needle 100 is expandable after exiting port 295. In some embodiments, the expanded portion is collapsible again upon withdrawal back into the sheath head 221.

It is expected that during the life of a patent maturing from this application many relevant biopsy needle features will be developed and the scope of the term "needle 100" is intended to include all such new technologies (unless incompatible with essential features of needles 100) a priori.

As used herein the term "about" refers to within ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A biopsy needle comprising:
   a distal portion, the distal portion comprising a laterally self-expanding piece built of one piece of springy material, wherein the one piece of springy material is split to form an aperture defining an interior space, and wherein the one piece of springy material is self-expanding due to the elasticity of the springy material to open the one piece of springy material to an open configuration expanding said interior space unless the one piece of springy material is constrained from self-expanding;
   a distal end including a sharpened leading edge of said one piece of springy material capable of penetrating tissue; and
   teeth along said self-expanding portion and formed from a portion of the one piece of springy material within the interior space;
   each of said teeth being oriented toward the aperture to catch tissue entering the interior space when the interior space is expanded within a surrounding tissue, and wherein each of said teeth is shaped to detach the caught tissue from said surrounding tissue upon withdrawal, wherein the laterally self-expanding piece of springy material, including the split to form an aperture defining an interior space, the sharpened leading edge, and the teeth along the self-expanding portion, is constructed from a single continuous piece of said springy material.

2. The needle of claim 1, wherein said laterally expandable distal portion, once laterally expanded to said open configuration, is laterally contractible to a closed configuration.

3. The needle of claim 2, wherein said expandable portion is laterally contractible from said open configuration to trap and hold said tissue.

4. The needle of claim 3, wherein said expandable portion contracts when said needle is retracted from tissue into which it had penetrated.

5. The needle of claim 3, wherein said expandable portion contracts when the relative position of said needle and a sheath changes, covering a portion of said needle with a distal portion of said sheath.

6. The needle of claim 1, comprising a base end with a releasable catch configured for tool-free mounting and unmounting to a receiving part.

7. The needle of claim 1, wherein said expandable portion comprises a plurality of spines moveable toward and away from each other along at least a portion of their length.

8. The needle of claim 7, wherein said spines are joined at their distal end and at their proximal end.

9. The needle of claim 8, wherein said spines distance themselves from each other when said expandable portion is laterally unconstrained, and approach each other when said expandable portion is laterally constrained.

10. The needle of claim 7, wherein at least some of said teeth along said self-expanding portion protrude from said spines into said interior volume, said interior volume being defined by said spines when said spines are distanced from each other in said open configuration, and said teeth being arranged along opposite said spines so that a point of each of said teeth is brought into closer proximity with an opposite of said spines, and the point being within said interior volume, when the self-expanding portion is laterally contracted to a closed configuration.

11. The needle of claim 1, wherein at least some of said teeth are so oriented as to have a sharp edge facing in a proximal direction, so as to catch and hold tissue when a distal portion of said needle is retracted from tissue into which it has been inserted.

12. The needle of claim 7, wherein said spines are operable to trap and hold tissue between said spines when said needle is inserted into tissue and is constrained to change from said open to a closed configuration.

13. The needle of claim 7, comprising more than two spines.

14. The biopsy needle of claim 1, comprising:
a sheath sized to contain at least a distal portion of said needle;
such that said needle is slideable distally and proximally within said sheath; and
said needle tends to assume said open or a closed configuration depending on where said expandable distal portion of said needle is positioned within said sheath.

15. The needle of claim 14, wherein said needle tends to assume said open configuration when said expandable distal portion extends beyond said sheath, and said expandable distal portion is constrained to assume said closed configuration when said expandable distal portion of said needle is positioned within said sheath.

16. The needle of claim 15, wherein said sheath comprises an elongated sheath body defining an interior lumen with an arcuate slot forming a continuum between said interior lumen of said sheath and an exterior aperture disposed laterally on the sheath body.

17. The needle of claim 16, wherein one or more walls of a surface of said lumen are formed with protrusions having heights sufficient to lift at least a portion of said needle away from adjacent portions of said lumenal surface.

18. The needle of claim 17, wherein protrusions of facing walls of the lumenal surface are arranged in staggered alternation along the length of the lumenal surface.

19. The needle of claim 14, comprising:
a sheath head at a distal end of said sheath;
said sheath head comprising a substantially tubular body;
wherein the wall of said body comprises at least one flap cut from the body of said sheath head, and protruding into a lumen defined by said body, such that said at least one flap comprises at least one guide protrusion contacted by said needle upon passage of a portion of said needle through said body.

20. The needle of claim 19, wherein said guide protrusion comprises a bearing surface having a polymer resin coating.

21. The needle of claim 19, wherein said at least one guide protrusion comprises at least two guide protrusions protruding into said lumen from opposite sides of said lumen.

22. The needle of claim 19, wherein:
said sheath head comprises an angle guide positioned at a distal end of the sheath head; and
said needle is constrained by contact with said angle guide to exit said sheath head at an angle oblique to the longitudinal axis of said sheath head.

23. The needle of claim 22, wherein said oblique exit angle is also determined by contact with a guide protrusion on a side of said needle opposite said angle guide.

24. The needle of claim 7, wherein each of said teeth comprises a respective cutting edge on a surface, wherein the surface extends between one of said plurality of spines and a sharpened point of the respective each of said teeth.

25. The needle of claim 1, wherein each of said teeth comprises a cutting edge, and the cutting edge tearingly cuts tissue when a distal portion of said needle is retracted from tissue into which it has been inserted.

26. The needle of claim 1, wherein each of said teeth comprises a cutting edge.

27. The needle of claim 1, wherein a cross-section transverse to a longitudinal extent of the constrained self-expanding portion has a flat shape.

28. The needle of claim 27, wherein the flat cross-section is substantially rectangular, interrupted by the split of said aperture, has a wide direction and a thin direction, and is self-expanding in the wide direction.

29. The needle of claim 1, wherein a cross-section transverse to a longitudinal extent of the constrained self-expanding portion has a substantially round shape, interrupted by splits of a plurality of said apertures.

30. The needle of claim 7, wherein a cross-section transverse to a longitudinal extent of each spine together with said oriented teeth along it has a flat or open-arched shape.

* * * * *